United States Patent
Chen et al.

(10) Patent No.: US 8,934,694 B2
(45) Date of Patent: Jan. 13, 2015

(54) MULTI-DIMENSIONAL ITERATIVE PHASE-CYCLED RECONSTRUCTION FOR MRI IMAGES

(75) Inventors: Nan-Kuei Chen, Cary, NC (US); Alexandru V. Avram, Bethesda, MD (US); Allen W. Song, Chapel Hill, NC (US); Trong-Kha Truong, Durham, NC (US)

(73) Assignee: Duke University, Durham, NC (US)

( * ) Notice: Subject to any disclaimer, the term of this patent is extended or adjusted under 35 U.S.C. 154(b) by 101 days.

(21) Appl. No.: 13/824,704

(22) PCT Filed: Oct. 3, 2011

(86) PCT No.: PCT/US2011/054523
§ 371 (c)(1),
(2), (4) Date: Mar. 18, 2013

(87) PCT Pub. No.: WO2012/047771
PCT Pub. Date: Apr. 12, 2012

(65) Prior Publication Data
US 2013/0182932 A1    Jul. 18, 2013

Related U.S. Application Data

(60) Provisional application No. 61/390,728, filed on Oct. 7, 2010, provisional application No. 61/418,134, filed on Nov. 30, 2010.

(51) Int. Cl.
*G06K 9/00* (2006.01)
*G06T 11/00* (2006.01)
*G01R 33/565* (2006.01)
*A61B 5/00* (2006.01)
*A61B 5/055* (2006.01)
(Continued)

(52) U.S. Cl.
CPC ........ *G06T 11/008* (2013.01); *G01R 33/56509* (2013.01); *G01R 33/56545* (2013.01); *A61B 5/0042* (2013.01); *A61B 5/055* (2013.01); *A61B 5/7207* (2013.01); *G01R 33/4824* (2013.01); *G01R 33/5611* (2013.01); *G01R 33/5616* (2013.01)
USPC .......................................................... 382/131

(58) Field of Classification Search
None
See application file for complete search history.

(56) References Cited

U.S. PATENT DOCUMENTS 5,270,654 A    12/1993 Feinberg et al.
6,150,814 A *  11/2000 Redpath et al. ............... 324/307
(Continued)

OTHER PUBLICATIONS

Anderson et al. "Analysis and correction of motion artifacts in diffusion weighted imaging", *Magn. Reson. Med.*, 32: 379-387, 1994.
(Continued)

*Primary Examiner* — Nancy Bitar
(74) *Attorney, Agent, or Firm* — Myers Bigel Sibley & Sajovec, P.A.

(57) ABSTRACT

Methods, systems, computer programs, circuits and workstations are configured to carry out image processing to generate MRI images with reduced aliasing artifacts (e.g., Nyquist and/or motion-induced image artifacts) by (a) electronically reconstructing a series of images using patient image data obtained from a patient MRI image data set by iteratively cycling through different estimated values of phase gradients in at least two dimensions; and (b) electronically selecting an image from the reconstructed images as having a lowest artifact level.

32 Claims, 12 Drawing Sheets

(51) Int. Cl.
 *G01R 33/48* (2006.01)
 *G01R 33/561* (2006.01)

(56) References Cited

U.S. PATENT DOCUMENTS

| | | | |
|---|---|---|---|
| 6,225,804 B1 * | 5/2001 | Lai | 324/309 |
| 6,717,406 B2 * | 4/2004 | Sodickson | 324/307 |
| 7,375,519 B2 | 5/2008 | Zur | |
| 7,689,539 B2 * | 3/2010 | Sjoblom et al. | 707/999.002 |
| 2001/0008376 A1 * | 7/2001 | Mock | 324/307 |
| 2004/0155652 A1 * | 8/2004 | Sodickson | 324/307 |

OTHER PUBLICATIONS

Bruder et al. "Image reconstruction for echo planar imaging with nonequidistant k-space sampling", *Magn. Reson. Med.*, 23:311-323, 1992.
Buonocore et al. "Ghost Artifact Reduction for Echo Planar Imaging Using Image Phase Correction", *MRM*, 38:89-100, 1997.
Buonocore et al. "Image-Based Ghost Correction for Interleaved EPI", *Magn. Reson, Med.*, 45:96-108, 2001.
Chen et al. "Two dimensional phase cycled reconstruction for inherent correction of EPI Nyquist artifacts", *Magn. Reson. Med.*, Date submitted by author, Sep. 22, 2010, 45 pages, 66(4): 1057-1066, Oct. 2011.
Chen et al., "Removal of EPI Nyquist ghost artifacts with two-dimensional phase correction", *Magnetic Resonance in Medicine*, 2004, pp. 1247-1253, vol. 51, Issue 6.
Clare S. "Iterative Nyquist Ghost Correction for Single and Multishot EPI using and Entropy Measure", *Proc. Intl. Soc. Mag. Reson. Med.*, 11, p. 1041, 2003.
Cuppen et al. "Magnetic resonance fast Fourier imaging", *Med. Phys.*, 13(2):248-253, 1986.
Foxall et al. "Rapid Iterative Reconstruction for Echo Planar Imaging", *Magn. Reson. Med.*, 42:541-547, 1999.
Frank et al. "High-efficiency, low distortion 3D diffusion tensor imaging with variable density spiral fast spin echoes (3D DW VDS RARE)", *NeuroImage*, vol. 49, Issue 2, Jan. 15, 2010, pp. 1510-1523.
Grieve et al. "Elimination of Nyquist Ghosting Caused by Read-Out to Phase-Encode Gradient Cross-Terms in EPI", *Magn. Reson. Med.*, 47:337-343, 2002.
Hennel et al. "Image-based reduction of artifacts in multishot echo-planar imaging", *J. Magn Reson*, 1998;134(2)206-213.
Hoge et al. "Robust EPI Nyquist Ghost Elimination via Spatial and Temporal Encoding", *Magn. Reson. Med.*, 64:1781-1791, 2010.
Hu et al. "Artifact Reduction in EPI with Phased-Encoded Reference Scan", *MRM*, 36:166-171, 1996.

International Preliminary Report on Patentability Corresponding to International Application No. PCT/US2011/054523; Date of Mailing: Apr. 18, 2013; 7 Pages.
International Search Report and Written Opinion Corresponding to International Application No. PCT/US2011/054523; Date of Mailing: Apr. 19, 2012; 11 Pages.
Jesmanowicz et al. "Phase Corrections for EPI Using Internal Reference Lines", *12th Annual Meeting of SMRM*, Book of Abstracts, Aug. 1993, p. 1239.
Karampinos et al. "High-Resolution Diffusion Tensor Imaging of the Human Pons With a Reduced Field-of-View, Multishot, Variable-Density, Spiral Acquisition at 3 T", *Magn. Reson. Med.*, 62:1007-1016, 2009.
Kellman et al. "Phased array ghost elimination", *NMR Biomed.*, 2006; 19:352-361.
Kim et al. "Automatic Correction of Echo-Planar Imaging (EPI) Ghosting Artifacts in Real-Time Interactive Cardiac MRI Using Sensitivity Encoding", *J. Magn. Reson. Imaging*, 2008;27:239-245.
Kuhara et al. "A Novel EPI Reconstruction Technique using Multiple RF Coil Sensitivity Maps", *8th Scientific Meeting and Exhibition, International Society for Magnetic Resonance in Medicine (ISMRM)*, Apr. 1-7, 2000, Denver, Colorado, USA, p. 154.
Li et al. "High-Resolution Diffusion-Weighted Imaging With Interleaved Variable-Density Spiral Acquisitions" *J. Magn. Reson. Imaging*, 2005;21:468-475.
Liu et al. "Self-Navigated Interleaved Spiral (SNAILS): Application to High-Resolution Diffusion Tensor Imaging", *Magn. Reson. Med.*, 52:1388-1396, 2004.
Madore et al. "Unaliasing by Fourier—Encoding the Overlaps Using the Temporal Dimension (UNFOLD), Applied to Cardiac Imaging and fMRI", *Magn. Reson. Med.*, 42:813-828, 1999.
Pruessmann et al. "SENSE: sensitivity encoding for fast MRI", *Magn. Reson. Med.*, Nov. 1999, 42(5):952-962.
Reeder et al. "Multi-Echo Segmented k-space Imaging: An Optimized Hybrid Sequence for Ultrafast Cardiac Imaging", *Magn, Reson. Med.*, 41:375-385, Feb. 1999.
Reeder et al. "Referenceless Interleaved Echo-Planar Imaging", *Magn. Reson. Med.*, 41(1):87-94, Jan. 1999.
Stone et al. "Accelerating Advanced MRI Reconstructions on GPUs", *J. Parallel Distrib Comput.*, 68(10): 1307-1318, Oct. 2008.
Truong et al. "Inherent Correction of Motion-Induced Phase Errors in Multishot Spiral Imaging using Iterative Phase Cycling", *ISMRM 19th Meeting and Exhibition*, Montreal, Quebec, Canada, May 7-13, 2011, 1 page.
Xiang et al. "Correction for Geometric Distortion and N/2 Ghosting in EPI by Phase Labeling for Additional Coordinate Encoding (PLACE)", *Magn. Reson. Med.*, 57:731-741, 2007.
Xu et al. "Robust 2D Phase Correction for Echo-Planar Imaging Under a Tight Field-of-View", *Proc. Intl. Soc. Mag. Reson. Med.*, 18, p. 5060, 2010.

* cited by examiner

MULTI-DIMENSIONAL ITERATIVE PHASE-CYCLED RECONSTRUCTION FOR MRI IMAGES

RELATED APPLICATIONS

This application is a 35 USC §371 national phase application of PCT/US2011/054523, International Filing Date Oct. 3, 2011, which claims the benefit of and priority to U.S. Provisional Application Ser. No. 61/390,728, filed Oct. 7, 2010, and U.S. Provisional Application Ser. No. 61/418,134 filed Nov. 30, 2010, the contents of which are hereby incorporated by reference as if recited in full herein.

BACKGROUND

Aliasing artifacts in MRI (originating from Nyquist artifacts, or intra-scan motion induced phase errors, among others) greatly reduce the quality of clinical MRI data. For example, it is well known that the inconsistency of k-space trajectories corresponding to opposite frequency-encoding gradient polarities in echo-planar imaging (EPI) results in Nyquist artifacts. Traditional techniques often only correct for phase errors along the frequency-encoding direction (i.e., 1D correction), which may still leave significant residual artifacts, particularly for oblique-plane EPI or in the presence of cross-term eddy current. As compared with 1D correction, two-dimensional (2D) phase correction methods can be much more effective in suppressing Nyquist artifacts. However, existing 2D correction methods can require extra reference scans and/or may not be generally applicable to different imaging protocols. Furthermore, it is believed that EPI reconstruction with 2D phase correction is susceptible to amplification of errors in reference scans. In addition, the intra-scan motion induced image-domain phase errors in segmented diffusion-weighted imaging (e.g., segmented diffusion-weighted EPI; segmented diffusion-weighted spiral imaging; segmented diffusion fast-spin echo imaging among others) result in severe aliasing artifacts in the acquired data. Furthermore, the large scale motion may result in k-space phase errors in segmented MRI acquisition (e.g. segmented EPI; segmented spiral imaging other others), producing aliasing artifacts in reconstructed images.

Other MRI pulse sequences/image acquisition types, with or without parallel imaging paradigms, can also be susceptible to Nyquist and/or motion-induced artifacts, and/or other types of aliasing artifacts.

SUMMARY OF EMBODIMENTS OF THE INVENTION

Embodiments of the present invention provide methods and systems with improved multi-dimensional phase correction techniques.

Embodiments of the present invention provide methods and systems with improved multi-dimensional iterative phase-cycled techniques for reducing aliasing artifacts (e.g., Nyquist artifacts, motion-induced artifacts among others).

Firstly, a series of images are generated from the same (original) dataset, by cycling through different possible values of phase errors using a multi-dimensional (e.g., 2D or 3D) reconstruction framework. Secondly, an image with the lowest artifact level is identified from images generated in the first step using criteria based on a predetermined parameter such as background energy (or potentially, entropy, or another detectable image signal parameter) in sorted and sigmoid-weighted signals.

The new methods are effective in removing Nyquist ghosts in single-shot and segmented EPI without acquiring additional reference scans and the subsequent error amplifications.

While the methods may be particularly suitable for single-shot and segmented EPI, the methods can be used with other pulse sequences, including, for example, gradient- and spin-echo imaging "GRASE" (proposed by Koichi Oshio and David Feinberg, see, e.g., U.S. Pat. No. 5,270,654, the contents of which is hereby incorporated by reference as if recited in full herein), spiral imaging, diffusion-weighted imaging "DWI" (popularly used for stroke imaging), fast spin-echo imaging and the like. For DWI, the correction methods can be carried for removing intersegment motion artifacts.

The invented phase-cycled reconstruction mathematical framework can be applied to suppress either image-domain multi-dimensional phase errors (e.g., Nyquist artifacts in EPI, motion-induced phase errors in DWI, among others) or k-space phase errors (e.g., due to large-scan intra-scan motion).

The invented methods can be applied to either non-parallel or parallel MRI pulse sequences, addressing aliasing artifacts originating from different sources.

The systems and/or methods may also be used for reconstructing archived image data to remove artifacts from prior acquired MRI images because no additional reference scans are needed.

The methods can be carried out using 3D phase corrections and are not limited to 2D phase correction.

The methods can be used with single channel receivers or multi-channel, parallel imaging techniques.

Particular embodiments are directed to methods for generating MRI images with reduced aliasing artifacts (e.g., Nyquist and/or motion-induced image artifacts among others). The methods include: (a) electronically reconstructing a series of images using patient (human or animal) image data obtained from a patient MRI image data set by iteratively cycling through different estimated values of phase gradients in at least two dimensions; and (b) electronically selecting an image from the reconstructed images as having a lowest artifact level.

The electronically reconstructing step can include, for a respective image slice, generating a first series of images using different possible phase gradient values along a frequency encoding direction and a second series of images using different possible values of phase gradients along a phase-encoding direction.

The method may optionally further include: (i) generating 1D image signal profiles associated with the reconstructed first and second series of images; and (ii) multiplying the 1D image signal profiles by a respective sigmoid-function weight. The electronically selecting step can thus be carried out using the sigmoid-weighted signals to identify phase error patterns.

In some embodiments, the 1D image signal profiles represent background energy in the reconstructed images.

The reconstructing step can be carried out without acquiring reference scans or requiring user input to identify background regions in the images.

The generating and identifying steps are typically carried out to suppress, correct or remove Nyquist ghost artifacts or motion-induced artifacts, or other types of aliasing artifacts from the patient images.

The reconstructing image step can be carried out using a defined phase range of values and a defined step size in a change in the estimated gradient values (i) along a frequency encoding direction and (ii) along a phase-encoding direction.

The reconstructing step may optionally include generating a first series of images using a selected first column of image data along a phase encoding direction located near a center of a field of view (FOV) at a defined location along a frequency encoding direction, then generating a second series of images using an adjacent second column.

Phase errors $\phi$ in the selected first column at location "y" along the phase encoding direction and location $x_0$ along the frequency-encoding direction, can be represented using at least $C_1$ and $C_2$ identified by the following equation:

$$\phi(x_0,y)=C_1+C_2\times y$$

where $C_1$ includes a contribution from both 1) a phase offset that is uniform for the whole 2D image and 2) nonlinear phase terms along the frequency-encoding direction; and $C_2$ represents a linear phase gradient along the phase encoding direction.

Alternatively, phase errors $\phi$ in the selected first column at location "y" along a phase encoding direction and location $x_0$ along a frequency-encoding direction, can be represented using the following equation:

$$\phi(x_0,y)=C_1+C_2\times y+C_3\times y^2$$

where $C_1$ includes a contribution from both 1) a phase offset that is uniform for a whole 2D image and 2) nonlinear phase terms along the frequency-encoding direction; $C_2$ represents a linear phase gradient along the phase encoding direction; and $C_3$ represents a nonlinear phase gradient along the phase-encoding direction.

In some embodiments, the generating step comprises generating multiple sets of 1D profile signals based on different possible values of $C_1$ cycled between $-\pi$ and $+\pi$ per pixel in a defined number "N" of steps and $C_2$ also cycled between $-\pi$ per pixel and $+\pi$ per pixel in the defined number "N" of steps to generate N×N 1D profile signals from the chosen column, where $C_1$ is a variable that includes a contribution from both 1) a phase offset that is uniform for a whole 2D image and 2) nonlinear phase terms along the frequency-encoding direction; $C_2$ represents a linear phase gradient along the phase encoding direction.

The reconstructing step optionally includes generating 1D MRI signal profiles using image data corresponding to a center FOV location. The identifying step may be carried out by: electronically sorting the 1D signal profiles in a defined order; multiplying the sorted signal profiles by a sigmoid function to define the sigmoid-weighted signals; electronically summing the weighted sorted signal profiles; and electronically identifying a lowest summed 1D signal profile as being an image with a lowest artifact level.

The reconstructing step can optionally be carried out so that a first series of reconstructed images is electronically evaluated using a first phase error range and iterative step size, and a second series of reconstructed images is subsequently electronically evaluated using a reduced phase error range and an adjusted step size.

The patient image data may be associated with at least one of the following pulse sequences: single-shot EPI, segmented EPI, parallel EPI, GRASE, multi-shot spiral imaging (with or without parallel acquisition), fast spin-echo imaging (with or without parallel acquisition), and integration of spin-warp imaging and EPI (with or without parallel acquisition).

Yet other embodiments are directed to methods of generating images from diffusion-weighted multi-shot spiral imaging with corrected motion-induced phase errors. The methods include: (a) obtaining multi-shot spiral acquired MRI patient image data; (b) iteratively phase cycling images of the obtained MRI patient image data reconstructed from central k-space; (c) selecting an image with a lowest level of signal intensity in a background region as the image with a least amount of aliasing; and (d) generating a (clinical) patient image based on the selected image.

The phase cycling can be carried out iteratively starting with a first range and step size at a first iteration, then reducing the range and adjusting the step size at a subsequent iteration.

The iterative phase cycling reconstructions can be carried out by reconstructing low resolution images from central k-space and the generating step is carried out to generate a higher resolution patient image.

The method may further include sorting pixel values associated with background energy in the reconstructed images in a defined order.

The sorting can be in an ascending order and the method can include summing a lowest percentage or number of pixels in each image to define a measure of background energy for that image.

This embodiment may be particularly suitable where the obtained patient image data are from diffusion-weighted spiral imaging and diffusion-weighted EPI.

Still other embodiments are directed to image processing circuits configured to electronically perform iterative phase-cycled image reconstruction in at least two dimensions on MRI patient image data sets (without requiring reference scans).

The circuit can be at least partially integrated into or in communication with at least one of: (a) a MR Scanner; (b) a clinician workstation; or (c) Picture Archiving and Communication System with archived patient image data.

The image processing circuit can be configured to apply a sigmoid-weighted factor to image signals associated with the reconstructed images and sort the weighted signals to identify phase pattern errors and correct for Nyquist artifacts.

The image processing circuit can be configured to reconstruct low resolution image slices by iteratively phase cycling images of the obtained MRI patient image data from central k-space, then select an image with a lowest level of signal intensity in a background region as the image with a least amount of aliasing, and generate a patient image based on the selected image.

The iterative phase cycling can be computationally carried out starting with a first range and step size at a first iteration, then reducing the range and adjusting the step size at a subsequent iteration.

Still other aspects are directed to MR image processing systems. The systems include a clinician workstation with a display and user interface comprising or being in communication with at least one image processing system that is configured to electronically perform multi-dimensional iterative phase-cycled image reconstruction on MRI patient image data sets to generate MRI images with reduced artifacts without a reference scan.

The system can further include an MR Scanner in communication with the workstation. Additionally or alternatively, the workstation can be in communication with a Picture Archiving and Communication System with archived patient MR image data.

Still other embodiments are directed to data processing systems that include a non-transient computer readable storage medium having computer readable program code embodied in the medium. The computer-readable program code comprising computer readable program code configured to perform multi-dimensional iterative phase-cycled image reconstruction on MRI patient image data sets to generate MRI images with reduced artifacts without a reference scan.

It is noted that aspects of the invention described with respect to one embodiment, may be incorporated in a different embodiment although not specifically described relative thereto. That is, all embodiments and/or features of any embodiment can be combined in any way and/or combination. Further, any feature or sub-feature claimed with respect to one claim may be included in another future claim without reservation and such shall be deemed supported in the claims as filed. Thus, for example, any feature claimed with respect to a method claim can be alternatively claimed as part of a system, circuit, computer readable program code or workstation. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

FIG. 3a shows 1D magnitude profiles of phantom EPI data (from one of eight coils). FIG. 3b shows a graph of sorted signals (solid line). FIG. 3c shows a graph of sigmoid weighted signals.

DETAILED DESCRIPTION

Figure 1:
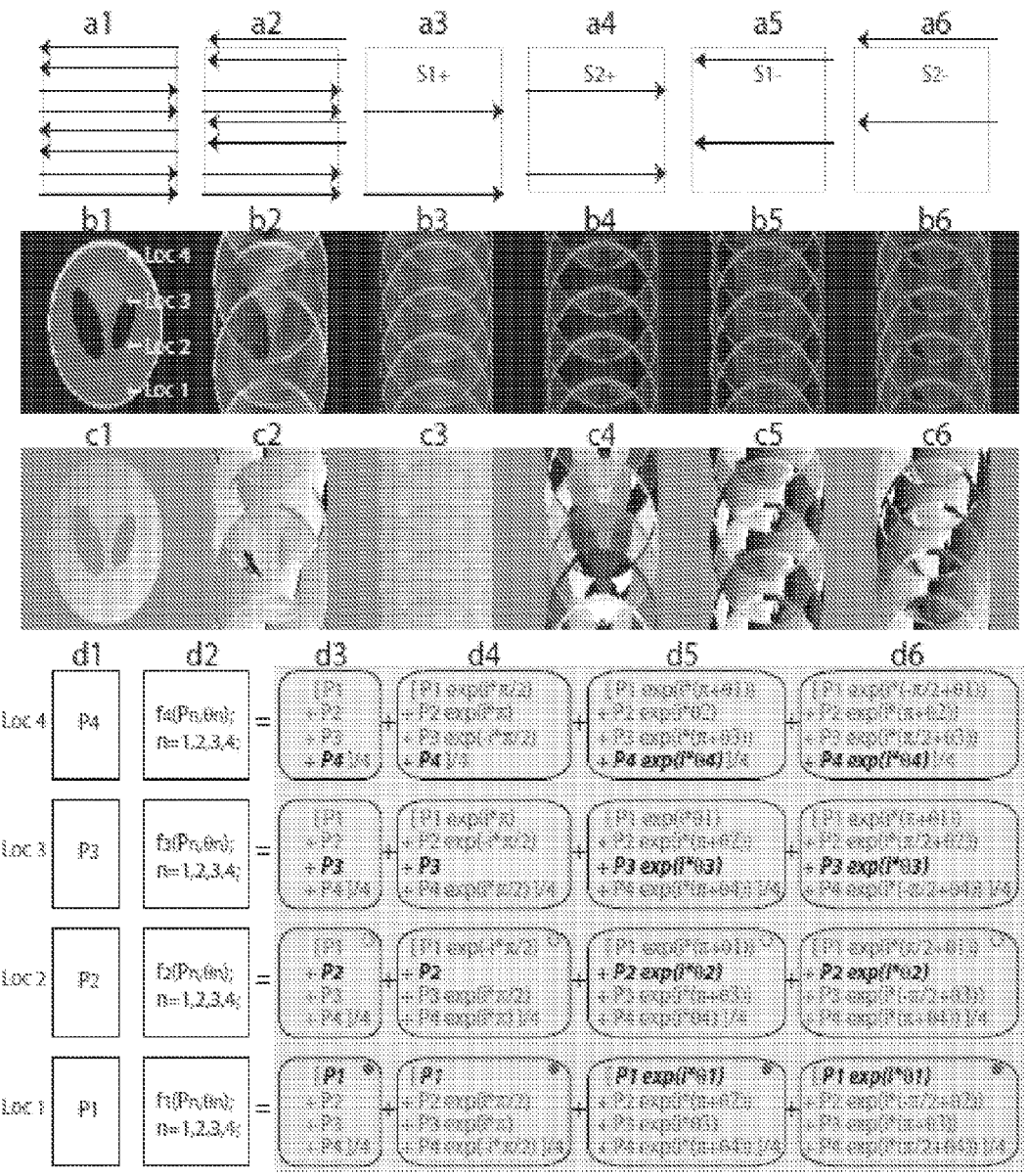
FIG. 1a illustrates schematic diagrams of ideal (a1) and distorted (a2) k-space trajectories of two-shot segmented EPI. The acquired k-space data can be decomposed into four parts as shown in (a3)-(a6).
FIGS. 1b and 1c illustrate magnitude and phase images reconstructed from k-space data (corresponding to (a1)-(a6)) with 2D FFT, respectively.
FIG. 1d illustrates the image-domain complex signals (corresponding to (a1)-(a6)) as a function of parent image signals and 2D phase errors.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various actions, steps or components and should not be limited by these terms. These terms are only used to distinguish one action, step or component from another action, step or component. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "circuit" refers to an entirely software embodiment or an embodiment combining software and hardware aspects, features and/or components (including, for example, a processor and software associated therewith embedded therein and/or executable by, for programmatically directing and/or performing certain described actions or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The term "archived" refers to electronically stored patient image data that can be accessed and reconstructed into patient images/visualizations/renderings. The diagnostic task of a clinician such as a radiologist can vary patient to patient and, accordingly so can the desired renderings or views of the medical images of the patient. In some visualization systems, a physician uses an interactive workstation that has a data retrieval interface that obtains the medical data for medical image renderings from electronic volume data sets to generate desired medical representations. Image visualizations using multi-dimensional MRI image data can be carried out using any suitable system such as, for example, PACS (Picture Archiving and Communication System). PACS is a system that receives images from the imaging modalities, stores the data in archives, and distributes the data to radiologists and clinicians for viewing.

The term "Direct Volume Rendering" or DVR is well known to those of skill in the art. DVR comprises electronically rendering a medical image directly from volumetric data sets to thereby display color visualizations of internal structures using 3D data. In contrast to conventional iso-surface graphic constructs, DVR does not require the use of intermediate graphic constructs (such as polygons or triangles) to represent objects, surfaces and/or boundaries. However, DVR can use mathematical models to classify certain structures and can use graphic constructs.

The terms "MRI scanner" or MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio. As is well known, the MR scanner can include a main operating/control system that is housed in one or more cabinets that reside in an MR control room while the MRI magnet resides in the MR scan suite. The control room and scan room can be referred to as an MR suite and the two rooms can be separated by an RF shield wall. The term "high-magnetic field" refers to field strengths above about 0.5 T, typically above 1.0 T, and more typically between about 1.5 T and 10 T. Embodiments of the invention may be particularly suitable for 1.5 T and 3.0 T systems, or higher field systems such as future contemplated systems at 4.0 T, 5.0 T, 6.0 T and the like. The methods and systems can also be applied to animal MRI data acquired from animal MRI scanners. The term "patient" refers to humans and animals.

The term "automatically" means that the operation can be substantially, and typically entirely, carried out without manual input, and is typically programmatically directed and/or carried out. The term "electronically" with respect to connections includes both wireless and wired connections between components.

The term "clinician" means physician, radiologist, physicist, or other medical personnel desiring to review medical data of a patient.

The term "reconstruction" is used broadly to refer to original or post-acquisition and storage and subsequent construction of image slices or images of an image data set.

The term "column-based" refers to image data that can be arranged in a matrix configuration of rows and columns which represent a location in either image-domain or k-space in Cartesian coordinates in two dimensions (e.g., a frequency encoded direction/dimension and a phase encoded direction/dimension) that can be iteratively evaluated by location defined by position with respect to a respective column and row. The attached figures demonstrate the application of invented phase-cycled reconstruction to correct for image-domain phase errors, and the column-based method refers to an image-domain column. It should be noted that, the invented phase-cycled reconstruction can also be directly applied to correct for k-space phase errors.

The term "iterative" and derivatives thereof refer to a computational procedure in which a cycle of operations is repeated using different phase values over defined ranges and incremental step sizes.

The term "low resolution" refers to images/image slices that are generated with a resolution that is less than a clinical diagnostic quality image, but typically with sufficient resolution to allow a background region to be visually distinguished from a target organ or tissue.

The terms "background" and "background region" are used interchangeably and refer to a location in an image/image slice that is outside the target object (e.g., outside an organ or tissue such as outside the brain or heart).

Each article, reference and patent cited or discussed herein is hereby incorporated by reference as if recited in full herein.

Embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

The k-space data of single-shot and segmented echo-planar imaging (EPI) are acquired with fast-switching frequency-encoding gradients of alternating polarities. Because of eddy currents, field inhomogeneities and other hardware imperfections, the k-space trajectories corresponding to different gradient polarities are often not well aligned, resulting in Nyquist artifacts in the reconstructed images.

Most Nyquist artifact reduction procedures to date are designed to correct for k-space trajectory misalignment along the frequency-encoding direction, and are referred to as one-dimensional (1D) correction in this paper. Using 1D correction procedures, the k-space misalignment is typically measured from non-phase encoded or phase encoded reference scans and subsequently used to correct for image-domain phase difference (a spatial function along the frequency-encoding direction) between 1D image-profiles corresponding to different frequency-encoding gradient polarities0. See, e.g., Bruder H, Fischer H, Reinfelder H E, Schmitt F. Image reconstruction for echo planar imaging with nonequidistant k-space sampling, Magn Reson Med 1992; 23(2):311-323 and Hu X, Le T H, Artifact reduction in EPI with phase-encoded reference scan. Magn Reson Med 1996; 36(1):166-171. Since the 1D phase difference may be estimated from just one or a few extra $k_y$ lines embedded in regular EPI sequences, the 1D reference scan does not reduce the imaging temporal resolution. See, e.g., Jesmanowicz A, Wong E C, Hyde J S. Phase correction for EPI using internal reference lines. 1993; New York, USA. p 1239.

It has also been shown that even without extra reference scans the 1D image-domain phase difference between opposite gradient polarities can actually be estimated directly from EPI data itself. See, e.g., Buonocore M H, Gao L. Ghost artifact reduction for echo planar imaging using image phase correction. Magn Reson Med 1997; 38(1):89-100; Hennel F. Image-based reduction of artifacts in multishot echo-planar imaging, J Magn Reson 1998; 134(2):206-213; and Buonocore M H, Zhu D C, Image-based ghost correction for interleaved EPI. Magn Reson Med 2001; 45(1):96-108. It has also been shown this information can be obtained by comparing images reconstructed from different subsets of the k-space data with parallel reconstruction. See, e.g., Kuhara S, Kassai Y, Ishihara Y, Yui M, Hamamura Y, Sugimoto H, A novel EPI reconstruction technique using multiple RF coil sensitivity maps, 2000; Denver, Colo., USA. p 154; Kim Y C, Nielsen J F, Nayak K S, Automatic correction of echo-planar imaging (EPI) ghosting artifacts in real-time interactive cardiac MRI using sensitivity encoding, J Magn Reson Imaging 2008; 27(1):239-245; and Kellman P, McVeigh E R, Phased array ghost elimination. NMR Biomed 2006; 19(3):352-361. Alternatively, Foxall et al. have shown that Nyquist artifacts in single-shot EPI can be minimized with an iterative phase cycling procedure without acquiring any reference scan. See, e.g., Foxall D L, Harvey P R, Huang J. Rapid iterative reconstruction for echo planar imaging, Magn Reson Med 1999; 42(3):541-547.

With iterative phase cycling, a series of images is first generated by using different possible values of phase difference from which a final image with the lowest artifact level can be identified based on background signal values. Recently a researcher has extended the iterative phase cycling to 1D phase correction for segmented EPI. See, e.g., Clare S, Iterative Nyquist ghost correction for single and multi-shot EPI using an entropy measure, 2008; Toronto, Canada. p 1041. Even though 1D correction techniques can usually reduce the majority of Nyquist artifacts, in many cases the residual aliasing after 1D correction remains significant. Particularly, when the image-domain phase difference (between sub-sampled images corresponding to opposite frequency-encoding gradient polarities) changes along both frequency- and phase-encoding directions (e.g., in oblique-plane imaging) (See, e.g., Reeder S B, Atalar E, Faranesh A Z, McVeigh E R. Referenceless interleaved echo-planar imaging, Magn Reson Med 1999; 41(1):87-94, or in the presence of cross-term eddy current (See, e.g., Grieve S M, Blamire A M, Styles P. Elimination of Nyquist ghosting caused by read-out to phase-encode gradient cross-terms in EPI, Magn Reson Med 2002; 47(2):337-343), the residual artifacts after 1D correction can be significant enough to make the reconstructed images unsuitable for clinical use. In these cases, a two-dimensional phase correction is needed.

Procedures for measuring and correcting for 2D phase errors differ from 1D phase mapping and correction in several ways. First, in terms of phase mapping, 2D phase errors in EPI data cannot be measured from a single over-sampled $k_y$ line, as used in conventional 1D correction procedures. Instead, it has been shown that 2D phase error measurements require additional full k-space reference scans at a significant cost of temporal resolution. See, e.g., Chen N K, Wyrwicz A M. Removal of EPI Nyquist ghost artifacts with two-dimensional phase correction. Magn Reson Med 2004; 51(6):1247-1253, Xiang Q S, Ye F Q. Correction for geometric distortion and N/2 ghosting in EPI by phase labeling for additional coordinate encoding (PLACE). See, Magn Reson Med 2007; 57(4):731-741, Hoge W S, Huan Tan H, Kraft R A. Robust EPI Nyquist Ghost Elimination via Spatial and Temporal Encoding; In Press. Magn Reson Med 2010, Xu D, King K F, Zur Y, Hinks R S. Robust 2D phase correction for echo planar imaging under a tight field-of-view; In Press. Magn Reson Med 2010; and U.S. Pat. No. 7,375,519. For example, U.S. Pat. No. 7,375,519 to Zur describes two-dimensional phase and magnitude corrections but requires a reference scan and does not use iterative processing. The contents of this patent are hereby incorporated by reference as if recited in full herein.

Even though it is possible to incorporate the 2D reference scan in dynamic EPI without increasing the total scan time (See, e.g., Hoge et al., supra), this imaging scheme is not generally applicable to different imaging protocols such as high-resolution imaging based on segmented EPI. Second, in terms of image correction, once 2D phase errors are measured from reference scans, artifact-free images need to be calculated by solving a set of linear equations through matrix inversion. If the acquired 2D phase maps are inaccurate (e.g., due to subject motion between reference and actual EPI scans) the error may be amplified depending on the condition number of the matrix inversion (See, e.g., Xu et al., supra).

Embodiments of the invention provide new procedures address these limitations and can estimate 2D phase errors and suppress Nyquist artifacts without the need of reference scans or user input. With these new procedures, the error amplification in previously reported with 2D phase correction procedures can be avoided. Furthermore, this technique can be generally applied to both single-shot and segmented EPI acquisitions as well as other image acquisition techniques including, for example, GRASE, spiral imaging and DWI, integrated spin-warp imaging (such as but not limited to SPGR) and EPI, and fast spin-echo.

Some MRI reconstruction procedures can perform the correction for 2D phase difference corresponding to opposite frequency-encoding gradient polarities assuming the 2D phase difference is known a priori. In contrast, embodiments of the instant invention provide an iterative phase cycling method from which a series of phase-corrected images is reconstructed using various possible 2D phase error values when no reference scan is available. The image with the lowest Nyquist artifact level can then be identified with criteria such as low background energy. In some embodiments, an image data processing technique can be used to significantly reduce the computational cost for iterative phase cycled reconstruction.

Reconstruction with Correction for 2D Phase Errors

Figure 2:
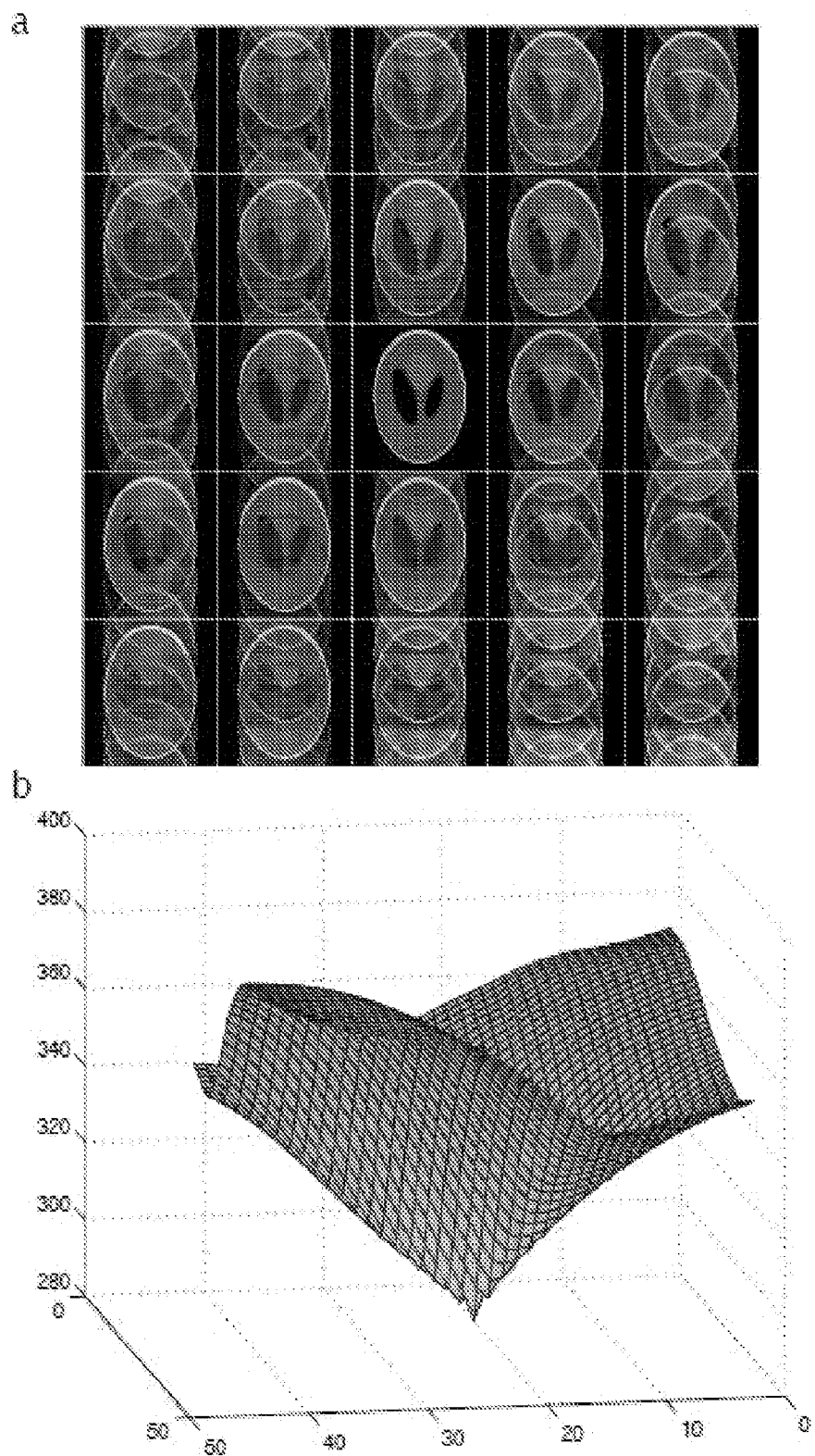
FIG. 2a shows a series of images reconstructed using Equation (2), cycling through different possible values of 2D phase errors.
FIG. 2b is a graph of energy level measured from the background for 2500 images reconstructed with 50 different phase gradient values along each of the directions.

FIGS. 1a1 and 1a2 schematically compare ideal and distorted k-space trajectories due to 2D phase differences corresponding to opposite frequency-encoding gradient polarities (using phase terms corresponding to positive frequency-encoding gradient as the reference), in a two-shot EPI acquisition. The reconstructed magnitude and phase images of a mathematical phantom (with displacement by 2.2 $k_x$-steps and 0.1 $k_y$-step between trajectories of opposite frequency-encoding gradient polarities) are shown in the corresponding columns in FIGS. 1b and 1c, respectively.

Figure 5:
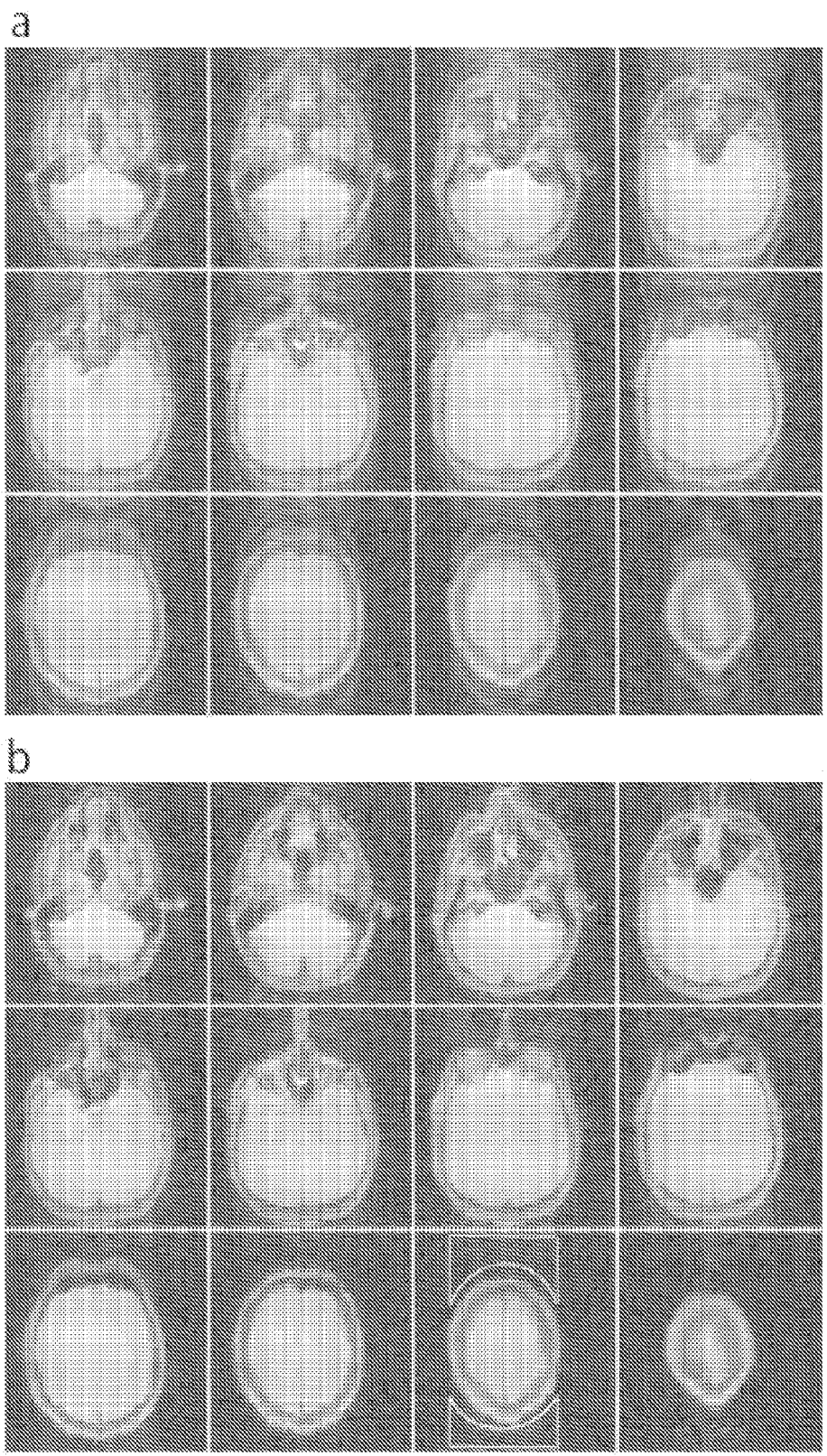
FIG. 5a shows four-shot segmented EPI, of 12 slices, obtained with 1D phase correction. The display scale was adjusted (power of 0.2) so that both residual Nyquist artifacts and background noises are visible.
FIG. 5b shows the images reconstructed with the iterative phase cycled process for 2-D phase correction as described herein according to embodiments of the present invention.
Figure 6:
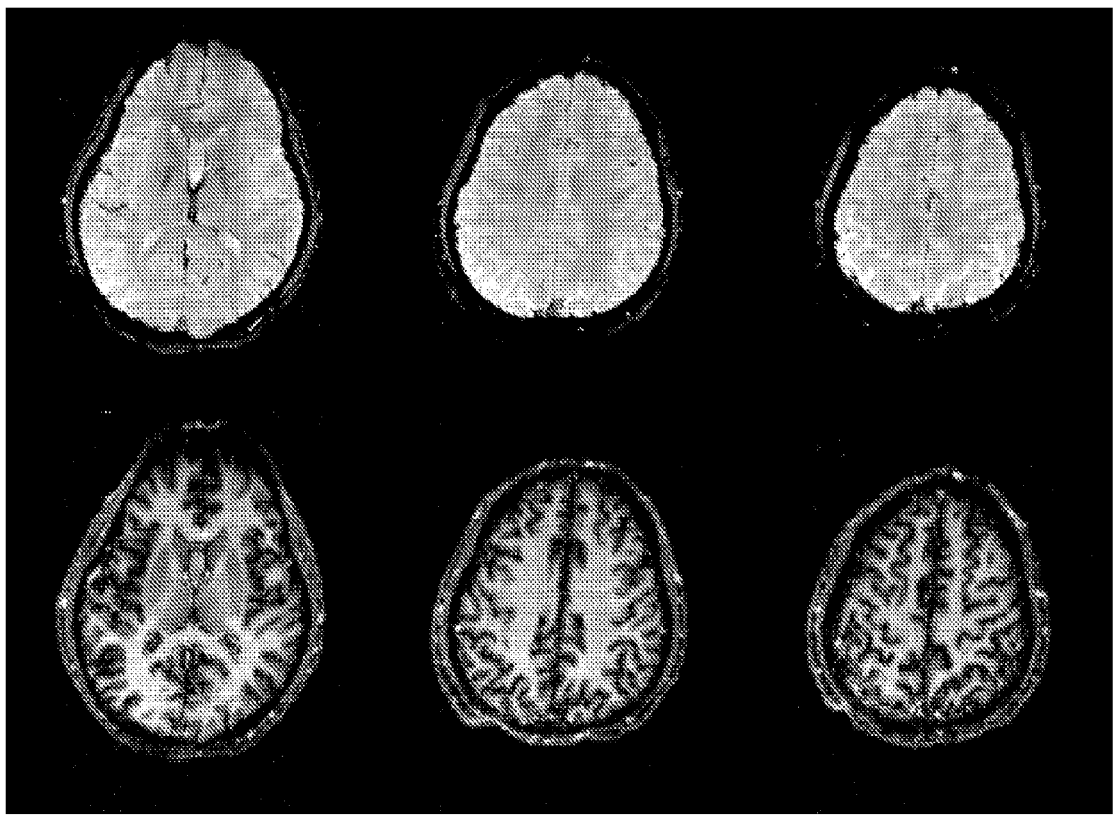
FIG. 6 shows top and bottom panels of images with 2D phase corrected T2*-weighted and inversion-recovery prepared high-resolution EPI images, respectively.

The two-shot EPI data (FIG. 1a2) can be decomposed into four subsets (or 2N subsets for N-shot EPI in general) corresponding to 1) segment #1/positive frequency-encoding gradient (i.e., S1+; shown in FIG. 1a3), 2) segment #2/positive gradient (i.e., S2+; shown in FIG. 1a4), 3) segment #1/negative gradient (i.e., S1−; shown in FIG. 1a5), and 4) segment #2/negative gradient (i.e., S2−; shown in FIG. 1a6). The summation of four sets of images reconstructed from 25% k-space subsets with 75% zero-filled (FIGS. 1b3 to 1b6; 1c3 to 1c6) can reproduce EPI images with Nyquist artifacts (FIGS. 1b2; 1c2). In two-shot EPI images (e.g., FIG. 1b2), signals from four voxels, separated by a quarter of FOV in the parent image (e.g., Loc 1 to 4 shown in FIG. 1b1) are mixed due to the aliasing effect. The goal of the 2D correction is thus to determine those signals, spatially separated in the parent image (FIG. 1d1) from the corrupted EPI data (FIG. 1d2).

In FIG. 1d $P_n$ represents the signal from location n of the artifact-free parent image and θ=θ(x,y) is the phase difference between the two images reconstructed from full k-space data corresponding to opposite frequency-encoding gradient polarities, e.g., measured from reference scans suggested in Chen et al., supra, or mathematically constructed before performing iterative phase cycled reconstruction described below.

Figure 3:
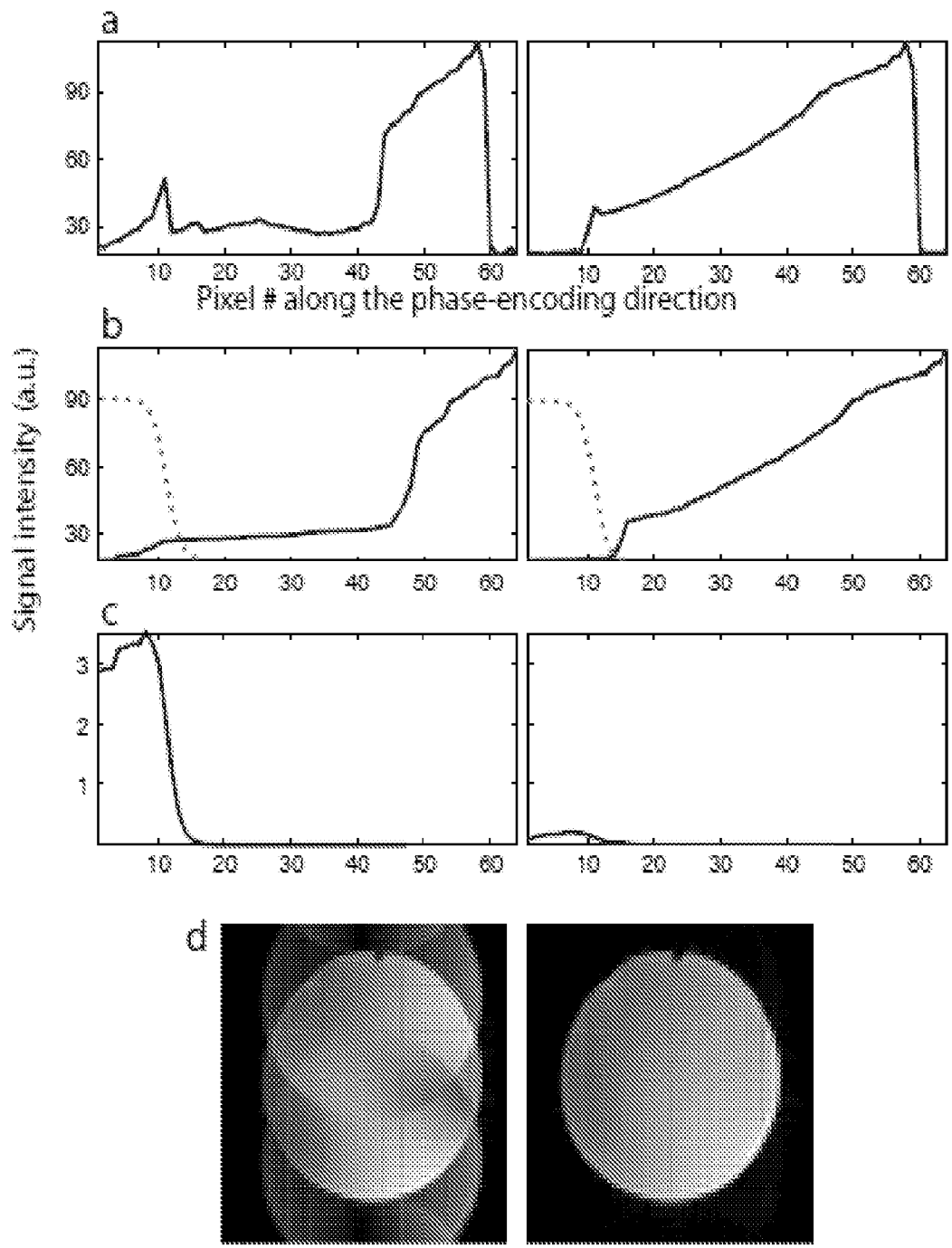
FIGS. 3a-3c are graphs of signal intensity versus pixel number along a phase-encoding direction for two different sets of C1 and C2 values (Equation 3).
FIG. 3d shows images that compare the uncorrected and phase-corrected two-shot EPI data, after combining data from all eight coils.
Figure 4:
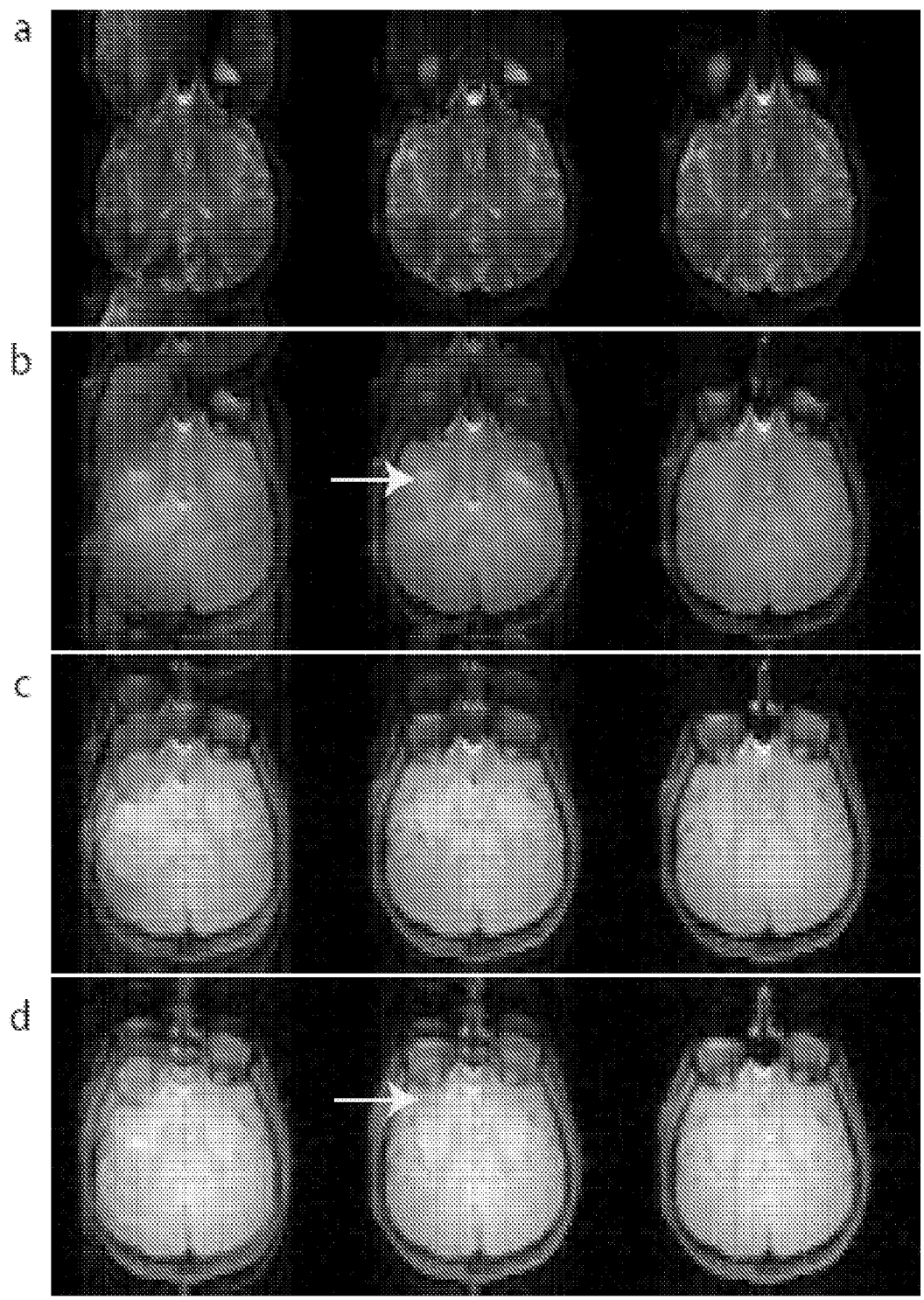
FIGS. 4a-4d show human brain EPI data in double oblique plane, acquired with 1, 2, 4 and 8 segments, respectively. The left column images were reconstructed without any phase correction. The middle column images were reconstructed with 1D phase correction. The right column images were reconstructed with the iterative phase cycled technique without the need of any reference scan according to embodiments of the present invention.

The signals from four locations (Loc 1 to 4) of four sub-sampled data sets (FIGS. 1b3 to b6; 1c3 to c6) are mathematically described in 16 rounded rectangles (with gray background) of FIG. 1d, with bold font representing parent image signals from the same location and regular font representing aliased signals from other three locations. As shown in FIG. 1d3, in each of the four locations the signal reconstructed from S1+ data is a linear combination of parent-image signals from all four locations. The signals reconstructed from S2+ data, because of the k-space trajectory shift along the phase-encoding direction (as compared with S1+), are the superpositions of parent and aliased images weighted by a certain phase modulation term per Fourier transformation. See, e.g., Madore B, Glover G H, Pelc N J. Unaliasing by fourier-encoding the overlaps using the temporal dimension (UNFOLD), applied to cardiac imaging and fMRI. Magn Reson Med 1999; 42(5):813-828, as shown in FIG. 1d4. The signals reconstructed from S1− and S2− (as shown in FIGS. 1d5 and 1d6 respectively) are modulated by two factors: 1) linear phase variation along the phase-encoding direction due to different k-space trajectories of the chosen subsets, and 2) nonlinear phase variations along both frequency- and phase-encoding directions due to eddy currents and other hardware imperfections.

If the 2D phase errors (e.g., $θ_n$ in FIG. 1d where n=1, 2, 3, 4) are known a priori, then the artifact-free signals (e.g., four unknowns: $P_n$; n=1, 2, 3, 4) can be determined from measured signals (e.g., 4 signals of location 1 from S1+, S2+, S1− and S2− data sets: 4 closed perimeter circles in FIG. 1b) with linear equations (e.g., in 4 rounded rectangles with solid dots near the bottom of in FIG. 1d). The linear equations corresponding to signals from other locations (e.g., location 2: indicated by rounded rectangles with circles one row above the bottom rectangles with the solid dots in FIG. 1d) are redundant with the equations corresponding to location 1. In general, for N-shot EPI, artifact-free parent-image signals can be obtained by solving Equation 1 or equivalently Equation 2 in its matrix form.

$$\upsilon = Ep \quad\quad \text{[Equation 1]}$$

$$\begin{bmatrix} u_1 \\ u_2 \\ \vdots \\ u_N \\ v_1 \\ v_2 \\ \vdots \\ v_N \end{bmatrix} = \frac{1}{2N} \begin{bmatrix} e^{i\frac{\pi}{N}\cdot 0\cdot 0} & e^{i\frac{\pi}{N}\cdot 0\cdot 1} & \cdots & e^{i\frac{\pi}{N}\cdot 0\cdot(2N-1)} \\ e^{i\frac{\pi}{N}\cdot 1\cdot 0} & e^{i\frac{\pi}{N}\cdot 1\cdot 1} & \cdots & e^{i\frac{\pi}{N}\cdot 1\cdot(2N-1)} \\ \vdots & \vdots & \ddots & \vdots \\ e^{i\frac{\pi}{N}\cdot(N-1)\cdot 0} & e^{i\frac{\pi}{N}\cdot(N-1)\cdot 1} & \cdots & e^{i\frac{\pi}{N}\cdot(N-1)\cdot(2N-1)} \\ e^{i\frac{\pi}{N}\cdot N\cdot 0}e^{i\phi_1} & e^{i\frac{\pi}{N}\cdot N\cdot 1}e^{i\phi_2} & \cdots & e^{i\frac{\pi}{N}\cdot N\cdot(2N-1)}e^{i\phi_{2N}} \\ e^{i\frac{\pi}{N}\cdot(N+1)\cdot 0}e^{i\phi_1} & e^{i\frac{\pi}{N}\cdot(N+1)\cdot 1}e^{i\phi_2} & \cdots & e^{i\frac{\pi}{N}\cdot(N+1)\cdot(2N-1)}e^{i\phi_{2N}} \\ \vdots & \vdots & \ddots & \vdots \\ e^{i\frac{\pi}{N}\cdot(2N-1)\cdot 0}e^{i\phi_1} & e^{i\frac{\pi}{N}\cdot(2N-1)\cdot 1}e^{i\phi_2} & \cdots & e^{i\frac{\pi}{N}\cdot(2N-1)\cdot(2N-1)}e^{i\phi_{2N}} \end{bmatrix} \begin{bmatrix} P_1 \\ P_2 \\ \vdots \\ P_{N-1} \\ P_N \\ P_{N+1} \\ \vdots \\ P_{2N} \end{bmatrix}. \quad \text{[Equation 2]}$$

where p in Equation 1 is a 2N×1 column vector with its elements $P_n$ representing un-aliased complex parent image signals separated by $$\frac{FOV_y}{2N}$$

along the phase-encoding direction; v in Equation 1 is a 2N×1 column vector with its elements $u_k$ and $v_k$ representing aliased image signals corresponding to the positive and negative frequency-encoding gradient polarities of the $k^{th}$ segment respectively (e.g., FIGS. 1b3 to b6); E in Equation 1 is a 2N×2N matrix, with $\phi_n$ in Equation 2 representing the 2D phase errors at location $P_n$. Note that it is sufficient to solve Equation 2 for only $$x_{size} \times \frac{y_{size}}{2N}$$

voxels of the reconstructed $u_k$ and $v_k$ images to reveal unknowns $P_n$ in the full FOV.

Iterative Phase Cycled Reconstruction and Minimization of Nyquist Ghost Artifact Equation 2 can be used to reconstruct artifact-free images if the 2D phase errors are known a priori such as in the case of reference scans (See, e.g., Chen et al., supra). However, the 2D reference scan is time-consuming, particularly for segmented EPI, and is not generally applicable to various applications (e.g., cardiac MRI and dynamic neuro-imaging among others). Furthermore, if the subjects move between reference and actual EPI scans, then phase errors may not be properly estimated and thus the residual artifact may still be pronounced in images reconstructed with Equation 2.

To address these limitations, the 2D EPI phase correction procedure can be integrated with an iterative phase cycled reconstruction without the need of a priori 2D phase information. The iterative reconstruction can generate/reconstruct a series of images along the lines of the matrix of Equation 2, cycling through different possible values of 2D phase errors. An image with the minimal Nyquist artifact is then identified based on effective criteria such as the background energy level. For example, images from different columns of FIG. 2a are reconstructed from the mathematical phantom (used to produce FIGS. 1b2 and 1c2) with five different possible values of phase gradient (centered at 2.2 kx-step displacement) along the frequency-encoding direction, and images from different rows are reconstructed with five different possible values of phase gradient (centered at 0.1 ky-point displacement) along the phase-encoding direction. The energy level measured from the background is plotted in FIG. 2b, for 2500 images reconstructed with 50 different phase gradient values along each of the directions. It can be seen that the Nyquist artifact is effectively eliminated only when the chosen phase gradient values match the simulation input.

In reality, 2D phase errors often include constant and nonlinear terms (particularly along the frequency-encoding direction) and thus cannot be described with linear phase gradients as in our mathematical phantom. As a result, it may be very time consuming when all possible nonlinear patterns of 2D phase errors are included in the iterative phase cycled reconstruction. Furthermore, it usually requires human input to identify background regions from which the energy level needs to be calculated and compared.

To address these issues, embodiments of the instant invention employ a column-based procedure to reduce the computation cost of iterative phase cycled reconstruction for Nyquist artifact removal without manually selecting background regions, as described below.

An iterative phase cycled reconstruction procedure can be implemented assuming that all 2D phase errors consist of 1) a spatially-independent phase offset, 2) nonlinear terms along the frequency-encoding direction, and 3) linear terms along the phase encoding direction. This model is highly sufficient to remove the Nyquist artifacts in phantom and human MRI (e.g., EPI) data. If needed, the procedure can also be extended to correct for nonlinear phase error terms along the phase-encoding direction, at a higher computation cost. The other assumption in the column-based procedure is that the scanned object is smaller than the FOV, which is valid for most MRI studies.

Specifically, an iterative phase cycling scheme can be used to process MRI signals from a single column along the phase-encoding direction located near the center of the FOV. The 2D phase errors in this chosen column (at location $x_0$ along the frequency-encoding direction) can be represented by Equation 3 ($x_0$ indicates the column location along the frequency encoding direction; for that chosen column, y indicates the voxel location along the phase-encoding direction).

$$\phi(x_0,y)=C_1+C_2\times y \quad \text{[Equation 3]}$$

where $C_1$ includes the contribution from both 1) a phase offset that is uniform for the whole 2D image, and 2) nonlinear phase terms along the frequency-encoding direction; $C_2$ represents the linear phase gradient along the phase encoding direction; and y represents the image-domain voxel location along the phase-encoding direction of the chosen column.

This equation can be used for pulse sequences that scan k-space data in Cartesian coordinates, including EPI, GRASE, integrated spin-warp imaging and EPI, and fast spin-echo. The phase-cycled reconstruction can be used to suppress not only phase errors originating from eddy current effect and gradient waveform distortions, but also phase inconsistency resulting from intra-scan subject motion among multiple segments corresponding to different RF pulse excitations, particularly in the presence of diffusion sensitizing gradients in DWI and DTI scans. Like multi-shot diffusion-weighted EPI, the multi-shot diffusion-weighted fast spin-echo imaging is also sensitive to intra-scan motion induced phase variation. The iterative phase cycled reconstruction can be applied to correct for the phase variation in fast spin-echo imaging as fast spin-echo imaging scans k-space data in Cartesian coordinates. For non-Cartesian coordinate pulse sequence (e.g., spiral imaging), this equation cannot be directly applied. As discussed below with respect to spiral imaging, multiple voxels overlap the reconstructed spiral imaging and a "point-spread function" evaluation process can be used instead of Equation 3.

Next, multiple sets of 1D profiles can be generated with Equation 2, based on different possible values of $C_1$ (cycled between $-\pi$ and $+\pi$ per pixel in 50 steps) and $C_2$ (between $-\pi$ per pixel and $+\pi$ per pixel in 50 steps). In other words, 2500 sets of 1D signals were generated from this chosen column. The signals are evaluated to choose the profile (from the N×N profiles, e.g., 2500 profiles) that corresponds to the lowest level of Nyquist artifact. For most of MRI applications, we usually have a rough idea about the size of the scanned object in reference to the FOV. For example, for brain MRI the object likely occupies 70% to 95% of the FOV. This knowledge is actually sufficient to help identify the 1D profile (from 2500 profiles) that is among the lowest artifact level in four steps: 1) The 1D signals generated from one of the phase patterns are sorted in an ascending order; 2) The sorted 1D profiles are multiplied by a sigmoid function, suppressing signals in ~80% of $FOV_y$; 3) The sorted and sigmoid-weighted signals are summed; and 4) The 1D profile with the lowest summed signal is identified from profiles corresponding to different combinations of coefficients $C_1$ and $C_2$.

For example, the left and right panels of FIG. 3a show the 1D magnitude profiles of phantom EPI data (from one of the eight coils) generated from two different sets of $C_1$ and $C_2$ values in Equation 3, respectively. The sorted signals are presented by solid curves in FIG. 3b, showing that more energy exists under the unsuppressed region of a sigmoid window (shown in a broken dashed line) in the left panel as compared with the right panel. The sigmoid-weighted signals are shown in FIG. 3c. The value obtained from summing all sorted and weighed signals is higher in the left panel than in the right panel. Based on the intensities of the summed signals, data in the left panels have a higher level of Nyquist artifact than data in the right panels. After identifying the 1D profile with the lowest artifact level from the phase cycled reconstructed data, the phase error patterns (represented by two coefficients $C_1$ and $C_2$ in Equation 3) in the chosen column can be determined.

For two columns that are located immediately next to the previously processed column, we can safely reduce the range of phase cycling when searching for optimal $C_1$ and $C_2$ values that best suppress the Nyquist artifact, since the 2D phase errors are slowly varying in space. In an exemplary implementation, the range of $C_1$ and $C_2$ cycling can be reduced by 5 times for each, so that only 100 profiles are generated through matrix inversion based on Equation 2. This procedure can then be extended to all the columns in the image slice, to the neighboring slices, and to the whole brain. Note that the 2D phase error patterns measured from one of the coils can actually be used to process the data obtained from other coils. FIG. 3d compares the uncorrected and phase-corrected two-shot EPI data using this procedure, after combining data from all eight coils.

In comparison to the scheme illustrated in FIG. 2, the developed column-based data processing procedure has a lower computation cost. The computation time to reconstruct a segmented EPI data set, of 64×64 matrix size, is about 3 sec per slice using a Matlab implementation in a Linux PC (CentOS; 2.6 GHz CPU; 8 GB memory).

An example of mathematical procedures that can be used to suppress the sorted signals in 80% (or $r_1$ in general) of FOV, assuming the length of the sorted 1D profile is L. First, a sigmoid-weighted array (S) of length 2×L is created using the following Equation:

$$S = 1 - \frac{1}{1+e^{-L_2}} \quad \text{[Equation 4]}$$

where $L_2$ is an integer-number array $(-L+1, -L+2 \ldots, L)$ of length 2×L.

Second, a new array (T), of length L, is chosen from subsets of the sigmoid-weighted array S with the following Equation:

$$T=S(L-r_2:2\times L-r_2-1) \quad \text{[Equation 5]}$$

where $r_2=L-\text{round}(L\times 80\%)$ or $r_2=L-\text{round}(L\times r_1)$ in general.

The sorted 1D profile can then be multiplied by the created T array to suppress 80% (or $r_1$ in general) of the signals.

Phase Cycled Reconstruction for Parallel EPI

Above, several mathematical equations (i.e., Equations 1 and 2) were described as particularly useful for conventional non-parallel EPI. However, aspects of the present invention can be used for parallel EPI, in which only subsets of the k-space data are acquired. For example, with parallel EPI of acceleration factor of 2 (commonly used for diffusion-tensor imaging), only about 50% of the k-space data are obtained. In this case, Equations 1 and 2 can be modified as shown below (for N-shot segmented EPI with the acceleration factor of M).

$$v = Ep \quad \text{[Equation 1']}$$

$$\begin{bmatrix} u_{M \times 0+1} \\ u_{M \times 1+1} \\ \vdots \\ u_N \\ v_{M \times 0+1} \\ v_{M \times 1+1} \\ \vdots \\ v_N \end{bmatrix} = \frac{1}{2N} \begin{bmatrix} e^{i\frac{\pi}{N}\cdot(M \times 0)\cdot 0} & e^{i\frac{\pi}{N}\cdot(M \times 0)\cdot 1} & \cdots & e^{i\frac{\pi}{N}\cdot(M \times 0)\cdot(2N-1)} \\ e^{i\frac{\pi}{N}\cdot(M \times 1)\cdot 0} & e^{i\frac{\pi}{N}\cdot(M \times 1)\cdot 1} & \cdots & e^{i\frac{\pi}{N}\cdot(M \times 1)\cdot(2N-1)} \\ \vdots & \vdots & \ddots & \vdots \\ e^{i\frac{\pi}{N}\cdot(N-M)\cdot 0} & e^{i\frac{\pi}{N}\cdot(N-M)\cdot 1} & \cdots & e^{i\frac{\pi}{N}\cdot(N-M)\cdot(2N-1)} \\ e^{i\frac{\pi}{N}\cdot N\cdot 0}e^{i\phi_1} & e^{i\frac{\pi}{N}\cdot N\cdot 1}e^{i\phi_2} & \cdots & e^{i\frac{\pi}{N}\cdot N\cdot(2N-1)}e^{i\phi_{2N}} \\ e^{i\frac{\pi}{N}\cdot(N+M)\cdot 0}e^{i\phi_1} & e^{i\frac{\pi}{N}\cdot(N+M)\cdot 1}e^{i\phi_2} & \cdots & e^{i\frac{\pi}{N}\cdot(N+M)\cdot(2N-1)}e^{i\phi_{2N}} \\ \vdots & \vdots & \ddots & \vdots \\ e^{i\frac{\pi}{N}\cdot(2N-M)\cdot 0}e^{i\phi_1} & e^{i\frac{\pi}{N}\cdot(2N-M)\cdot 1}e^{i\phi_2} & \cdots & e^{i\frac{\pi}{N}\cdot(2N-M)\cdot(2N-1)}e^{i\phi_{2N}} \end{bmatrix} \begin{bmatrix} P_1 \\ P_2 \\ \vdots \\ P_{N-1} \\ P_N \\ P_{N+1} \\ \vdots \\ P_{2N} \end{bmatrix}$$

[Equation 2']

where p in Equation 1' is a 2N×1 column vector with its elements $P_n$ representing un-aliased complex parent image signals separated by $$\frac{FOV_y}{2N}$$

along the phase-encoding direction; v in Equation 1' is a $$\frac{2N}{M} \times 1$$

column vector with its elements $u_k$ and $v_k$ representing aliased image signals corresponding to the positive and negative frequency-encoding gradient polarities of the $k^{th}$ segment; E in Equation 1' is a $$\frac{2N}{M} \times 2N$$

matrix, with $\phi_n$ in Equation 2' representing the 2D phase errors at location $P_n$. Note that Equations 1' and 2', with 2N unknowns and only $$\frac{2N}{M}$$

linear equations, are under-determined. Therefore, the proposed phase-cycled reconstruction can be integrated with the published SENSE algorithm to remove EPI Nyquist artifacts through solving the Equation 6 shown below. For a description of SENSE, see, Pruessmann et al. SENSE: sensitivity encoding for fast MRI, Magn Reson Med. 1999 November; 42 (5):952-62.

[Equation 6]

$$\begin{bmatrix} u^w_{M \times 0+1} \\ u^w_{M \times 1+1} \\ \vdots \\ u^w_N \\ v^w_{M \times 0+1} \\ v^w_{M \times 1+1} \\ \vdots \\ v^w_N \end{bmatrix} = \frac{1}{2N} \begin{bmatrix} S^w_1 e^{i\frac{\pi}{N}\cdot(M \times 0)\cdot 0} & S^w_2 e^{i\frac{\pi}{N}\cdot(M \times 0)\cdot 1} & \cdots & S^w_{2N} e^{i\frac{\pi}{N}\cdot(M \times 0)\cdot(2N-1)} \\ S^w_1 e^{i\frac{\pi}{N}\cdot(M \times 1)\cdot 0} & S^w_2 e^{i\frac{\pi}{N}\cdot(M \times 1)\cdot 1} & \cdots & S^w_{2N} e^{i\frac{\pi}{N}\cdot(M \times 1)\cdot(2N-1)} \\ \vdots & \vdots & \ddots & \vdots \\ S^w_1 e^{i\frac{\pi}{N}\cdot(N-M)\cdot 0} & S^w_2 e^{i\frac{\pi}{N}\cdot(N-M)\cdot 1} & \cdots & S^w_{2N} e^{i\frac{\pi}{N}\cdot(N-M)\cdot(2N-1)} \\ S^w_1 e^{i\frac{\pi}{N}\cdot N\cdot 0}e^{i\phi_1} & S^w_2 e^{i\frac{\pi}{N}\cdot N\cdot 1}e^{i\phi_2} & \cdots & S^w_{2N} e^{i\frac{\pi}{N}\cdot N\cdot(2N-1)}e^{i\phi_{2N}} \\ S^w_1 e^{i\frac{\pi}{N}\cdot(N+M)\cdot 0}e^{i\phi_1} & S^w_2 e^{i\frac{\pi}{N}\cdot(N+M)\cdot 1}e^{i\phi_2} & \cdots & S^w_{2N} e^{i\frac{\pi}{N}\cdot(N+M)\cdot(2N-1)}e^{i\phi_{2N}} \\ \vdots & \vdots & \ddots & \vdots \\ S^w_1 e^{i\frac{\pi}{N}\cdot(2N-M)\cdot 0}e^{i\phi_1} & S^w_2 e^{i\frac{\pi}{N}\cdot(2N-M)\cdot 1}e^{i\phi_2} & \cdots & S^w_{2N} e^{i\frac{\pi}{N}\cdot(2N-M)\cdot(2N-1)}e^{i\phi_{2N}} \end{bmatrix} \begin{bmatrix} P_1 \\ P_2 \\ \vdots \\ P_{N-1} \\ P_N \\ P_{N+1} \\ \vdots \\ P_{2N} \end{bmatrix}$$

where $S_n^w$ represents the coil sensitivity profile for coil number w at location n; and $u_k^w$ and $v_k^w$ represent aliased image signals, measured from coil number w, corresponding to the positive and negative frequency-encoding gradient polarities of the $k^{th}$ segment. Note that, when including data from all W coils, there are 2N unknowns and $$\frac{2N}{M} \times W$$

linear equations in Equation 6, which is solvable when W>M. It should also be noted that Equation 6 just demonstrates one of many possible implementations for integrating phase-cycled reconstruction and parallel imaging. In general, in particular embodiments, the phase-cycled reconstruction provides a new mathematical framework for further reducing aliasing artifacts in parallel MRI (and is not limited to parallel EPI).

Methods

Because the image processing does not require additional reference scans, the new multi-dimensional phase correction technique can be applied to retrospectively suppress Nyquist artifacts in multiple phantom and human MRI (e.g., EPI) data sets previously acquired with different scan parameters. Examples of different scan parameters include, spin-echo and gradient-echo EPI, single-shot and segmented EPI, full-Fourier and partial-Fourier EPI, fast spin-echo, quadrature coil and phased array coils; 1.5 T and 3 T. The new multi-dimensional (e.g., 2D) phase correction method can consistently and better suppress Nyquist artifacts than the 1D correction, particularly in EPI data acquired in oblique planes.

The first set of human brain EPI data presented here was acquired from a healthy volunteer at 3 Tesla with a quadrature head coil. Four whole-brain images were obtained with spin-echo EPI consisted of 1, 2, 4 and 8 segments. Other scan parameters included: FOV=24 cm×24 cm, matrix size=64×64, slice thickness=4 mm, TR=2 sec, and TE was set to the minimal value available (34, 26, 20, and 16 msec respectively). The subject's head position was tilted from the ideal position (yaw: ~20°; pitch: ~10°), so that a double-oblique plane was chosen to generate images that correspond to a regular axial-plane. The acquired data were corrected with either conventional 1D correction (See, e.g., Reeder et al.), or the new 2D correction method. The sigmoid function was chosen to suppress signals in 85% of the FOV (i.e., assuming that the scan objects occupied 85% of the FOV). The reconstructed images were then compared in terms of the residual artifact level in the background.

The second and third sets of human brain EPI data were obtained from a healthy volunteer at 3 Tesla with an eight-channel coil. T2*-weighted images were acquired with gradient-echo full-Fourier EPI of 2 segments, and scan parameters included: FOV=24 cm×24 cm, matrix size=160×160, slice thickness=2.4 mm, TR=3 sec, and TE=35 msec. T1-weighted images were acquired with inversion-recovery prepared spin-echo partial-Fourier EPI of 2 segments, and scan parameters included: FOV=24 cm×24 cm, matrix size=160×160, slice thickness=2.4 mm, inversion time=1 sec, TR=5 sec, and TE=67 msec. These two sets of images have identical voxel size (1.5 mm×1.5 mm×2.4 mm) and distortion patterns, and can be directly compared with each other for multi-contrast evaluation.

For T1-weighted partial-Fourier EPI, the 2D correction was performed in data from one of the coils, and phase errors were characterized using the iterative phase cycling scheme described above. The derived information was then applied to remove Nyquist artifacts in data from each of the eight coils using Equation 2. The phase corrected partial-Fourier data were extended to full-Fourier data using Cuppen's algorithm. See, e.g., Cuppen J J, Groen J P, Konijn J. Magnetic resonance fast Fourier imaging, the contents of which are hereby incorporated by reference as if recited in full herein. Med Phys 1986; 13(2):248-253, Data from multiple coils were then combined, with sum-of-squares, to form a composite magnitude image. A very similar 2D phase correction procedure was applied to remove Nyquist artifacts in T2*-weighted full-Fourier EPI data, except that the Cuppen's algorithm was not needed for full-Fourier images.

Results

The human brain EPI data in double oblique plane, acquired with 1, 2, 4, and 8 segments are shown in FIGS. 4a to 4d, respectively. The images in the left column of FIG. 4 were reconstructed directly from the k-space data with Fourier transform without any phase correction, and show strong Nyquist artifacts in all four data sets. The images in the middle column of FIG. 4 were reconstructed with 1D phase correction and exhibit significantly reduced artifacts as compared with uncorrected images. However, residual artifacts remain visible and may interfere with the parent image signals, as indicated by arrows. The images in the right column of FIG. 4 were reconstructed with the new 2D phase correction technique without the need of any reference scan. It can be seen that Nyquist artifacts are much better suppressed with 2D correction in comparison to those with the conventional 1D correction method.

The display scale of the four-shot segmented EPI obtained with 1D and 2D correction were then adjusted (with power of 0.2) so that both residual Nyquist artifacts and background noises are visible. As shown in FIG. 5a, the 1D phase corrected images have noticeable residual artifacts in 12 chosen slices. On the other hand, using the developed 2D phase correction method, the majority of the Nyquist artifacts can be suppressed more effectively (FIG. 5b). The ghost-to-noise ratios measured from the manually chosen ROIs in all 12 slices, e.g., the yellow area (ghost) and the red area (noise) for 1 of the slices, were 4.6 in 1D phase-corrected images, and 2.3 for 2D phase-corrected images.

Notably, even though a single sigmoid function was used to suppress signals in 85% of the FOV for all of the slices, the residual artifacts are low in almost all of these 12 slices in FIG. 5b regardless of the object size in reference to the FOV. The image quality obtained with different sigmoid profiles have been evaluated (e.g., to suppress signals in 70%, 80% or 90% of the FOV) and similar artifact suppression efficiency can still be reliably achieved.

The phase-corrected T2*-weighted and the inversion-recovery prepared EPI images, of three selected slices, are shown in the top and bottom rows of FIG. 6 respectively. It can be seen that the achieved image quality appears similar to that obtained with conventional spin-warp imaging. It is expected that the image quality improvement with this Nyquist artifact removal technique will be important for clinical utilization of EPI techniques.

Artifact Removal for Integrated Spin-Warp Imaging and EPI

It has been shown that the EPI readout gradient waveforms can be embedded into the conventional spin-warp imaging, such as spoiled gradient recalled (SPGR), to improve the scan efficiency and throughput. See, e.g., Reeder et al., Multi-echo segmented k-space imaging: an optimized hybrid sequence for ultrafast cardiac imaging, Magn. Reson Med. 1999, February; 41 (2): 375-385, the contents of which are hereby incorporated by reference as if recited in full herein. The new phase-cycled reconstruction can be directly applied to remove the Nyquist artifacts in the integrated spin-warp imaging and EPI, allowing MRI of high-quality and high-throughput.

Discussion

It has been shown that when the phase error terms vary spatially along both frequency- and phase-encoding directions the resultant Nyquist artifacts in EPI cannot be effectively removed with 1D phase correction. This is particularly problematic for oblique plane EPI, in which two or more physical gradients are combined to generate fast-switching frequency-encoding gradient. Oblique-plane scans are regularly used for brain imaging (e.g., parallel to anterior commissure-posterior commissure line) and cardiac EPI (e.g., perpendicular to the long cardiac axis) among others. Therefore, we expect that our new 2D phase correction for effective EPI Nyquist artifact removal will prove valuable for many clinical applications.

The 2D phase errors can be completely characterized with iterative phase cycling without the need for an extra reference scan. It should be noted that our new technique is also compatible with reference-scan based phase correction. For example, the 1D reference scan (e.g., embedded in EPI scans without scan time penalty (3)) can be used to first correct for the global phase offset and 1D nonlinear phase variation along the frequency-encoding direction (i.e., $C_1$ in Equation 3). The 1D phase corrected EPI data can then undergo the same iterative phase cycled reconstruction and 2D phase correction. In this way, the range of the phase cycling, and thus the computation cost, can potentially be significantly reduced.

In addition to the strategy described in the previous paragraph, the computation time of iterative phase cycled reconstruction may also be reduced using GPU based processing (rather than CPU) (See, e.g., Stone S S, Haldar J P, Tsao S C, Hwua W-mW, Sutton B P, Liang Z-P. Accelerating advanced MRI reconstructions on GPUs. J Parallel Distrib Comput 2008; 68:1307-1318 and parallel computation. Furthermore, the computation time may be further reduced if the algorithm is implemented in another platform, e.g., C instead of Matlab.

In Equation 3, it was assumed that the 2D phase errors vary linearly along the phase-encoding direction, and we found that this model is sufficient to remove the Nyquist artifacts in our EPI data. If there exists nonlinear phase gradient along the phase-encoding direction, then we may extend the linear model in Equation 3 to include nonlinear terms.

$$\phi(x_0, y) = C_1 + C_2 x y + C_3 x y^2 \qquad [\text{Equation 3'}]$$

Iterative phase cycled reconstruction based on this model obviously requires a higher computation cost. In this case, the strategies for reducing the computation time, as described in the previous two paragraphs, will be important.

Single-shot EPI has been a powerful tool for functional MRI, dynamic contrast enhanced imaging, and diffusion tensor imaging. On the other hand, even though segmented EPI has great potential for producing multi-contrast data, it has not yet been widely used clinically, in part due to the challenges in suppressing the undesirable Nyquist artifacts. With the effective artifact correction technique shown in this paper, segmented EPI based structural imaging may potentially provide image quality comparable to spin-warp imaging but with shorter scan time.

The developed phase cycled reconstruction scheme may be further extended to identify and remove artifacts originating from other types of intra-scan phase inconsistencies, in addition to the Nyquist artifacts in EPI. For example, motion-induced phase variations in diffusion-weighted segmented EPI may be estimated and corrected with our new technique, without requiring a navigator echo.

The phase cycled reconstruction may be able to address various types of phase related artifacts in EPI and parallel-EPI.

Inherent Correction of Motion-Induced Phase Errors in Multishot Spiral Imaging using Iterative Phase Cycling Spiral imaging has recently emerged as an alternative to echo-planar imaging for diffusion tensor imaging (DTI) because of its efficient k-space coverage and low sensitivity to flow artifacts. See, e.g., Liu, MRM 2004; 52:1388; Karampinos, MRM 2009; 62:1007; and Frank, NeuroImage 2010; 49:1510, the contents of which are hereby incorporated by reference as if recited in full herein. Multishot spiral trajectories are typically required to achieve a high resolution while maintaining a short readout duration to minimize off-resonance effects. However, shot-to-shot phase variations induced by motion in the presence of diffusion gradients lead to severe artifacts. Variable-density spiral trajectories can be used to generate a low-resolution phase estimate from the oversampled central k-space for each shot and correct for such artifacts. See, Liu, Karampinos, Frank as cited above. However, the readout duration is increased by up to 70%, resulting in a longer scan time and a higher sensitivity to off-resonance effects. See, Li, JMRI 2005; 21:468, the contents of which are hereby incorporated by reference as if recited in full herein. The iterative phase cycling methods can correct for motion-induced phase errors in multishot spiral imaging that does not require any additional navigator, thus allowing a shorter scan time as compared to variable-density spiral acquisitions.

Methods

Figure 7:
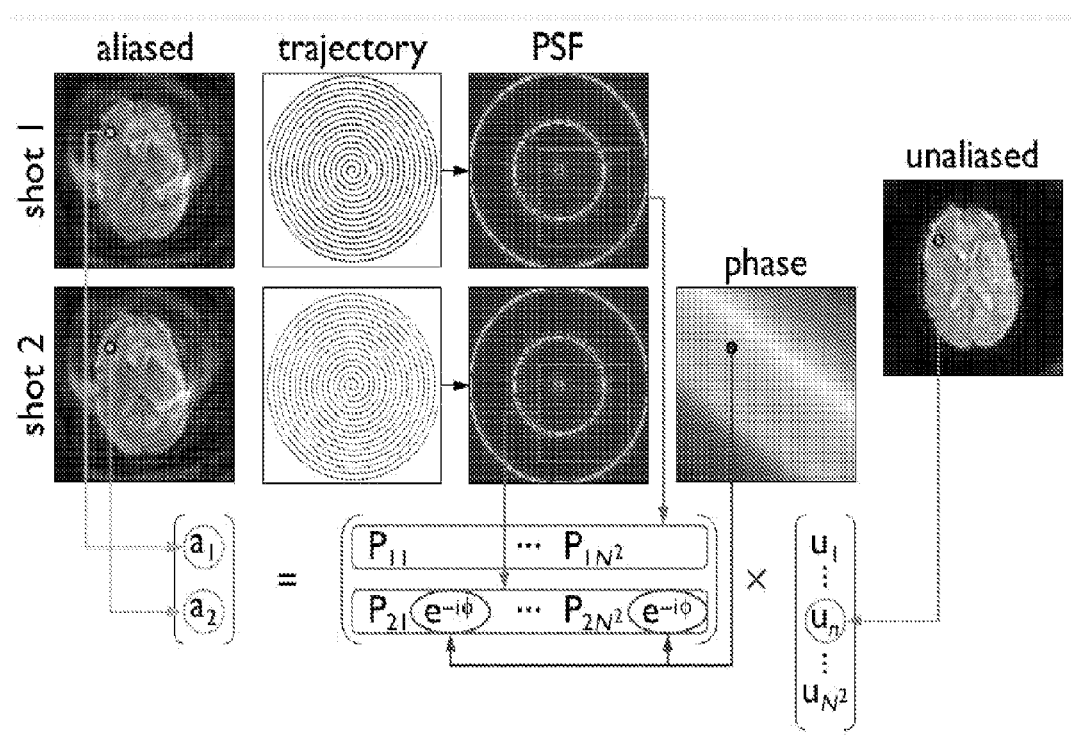
FIG. 7 is a diagram that illustrates the relationship between the aliased and unaliased images, the PSFs, and the motion-induced phase error according to embodiments of the present invention.

For simplicity, a 2-shot spiral acquisition is considered with an N×N matrix size, but extension to any number of shots is straightforward. For each shot m, the point spread function is computed as: $\text{PSF}_m(x, y) = \Sigma_n \text{DCF}(n) \exp\{i 2\pi [x k_x(n,m) + y k_y(n,m)]\}$, where DCF is the density compensation function, $(k_x, k_y)$ the spiral k-space trajectory, and $(x, y)$ the spatial position on a $(2N-1)^2$ grid. The k-space data from each shot is then reconstructed separately (by zero-filling the missing data), resulting in aliased images due to undersampling. For each pixel $(x_0, y_0)$, the relation between these images and the unaliased image to be reconstructed can be expressed as:

$$a = E \cdot u \qquad [\text{Equation 7}],$$

where a is a 2×1 array containing the pixel values from the aliased images and u is a $N^2 \times 1$ array whose $(x_0, y_0)^{th}$ element contains the pixel value from the unaliased image (FIG. 7).

In the absence of motion, E is a $2 \times N^2$ matrix whose rows contain the N×N subsets $(N-x_0+1:2N-x_0, N-y_0+1:2N-y_0)$ of $\text{PSF}_1$ and $\text{PSF}_2$ (red squares). In the presence of motion, the second row of E is multiplied by $\exp[-i\phi(x_0, y_0)]$, where $\phi$ is the motion-induced phase error between the two shots. Thus, if $\phi$ is known, the unaliased image can be determined by solving Eq. [7] for each pixel.

However, since $\phi$ is generally unknown, we use a phase cycling method, which consists in reconstructing a series of images using different $\phi$ values and choosing the image with the least amount of aliasing. One can assume that $\phi$ is spatially linear, i.e., $\phi(x, y) = \phi_0 + x g_x + y g_y$, where $\phi_0$ is a global phase offset and $(g_x, g_y)$ are linear phase gradients along $(x, y)$, and cycle through different values of $\phi_0$, $g_x$, and $g_y$. This model is sufficient to correct for phase errors induced by rigid-body motion (Anderson, MRM, 1994; 32:379), but can easily be extended to correct for nonlinear phase errors induced by non-rigid motion.

The image with the least amount of aliasing is chosen as the one with the lowest signal intensity in the background (i.e., outside the object). To avoid having to manually define the background region, the pixel values of each image can be sorted in a desired order such as descending or ascending order, typically the latter and the lowest 25% can be summed to yield the background energy. As the energy does not need to be computed in the entire background, this threshold is not critical and can typically range from between about 5% to 50%.

Because cycling through all possible values of φ requires a relatively long computation time, two strategies can speed up the reconstruction. First, the phase cycling can be performed only on low-resolution images reconstructed from the central k-space, which remains very effective as long as the resolution is sufficient to distinguish the background from the object. Once φ is known, the final image can be reconstructed at full resolution. Second, the phase cycling is performed iteratively, starting with a large range and step size for $φ_0$, $g_x$, and $g_y$. Once an estimate for φ is found, both the range and step size are reduced at the next iteration. The initial step size should be small enough to avoid local minima in the background energy.

As a proof-of-concept, a healthy volunteer was studied/evaluated on a 3 T GE Scanner using a 2-shot spiral pulse sequence with TR/TE=1580/30 ms, FOV=24.3 cm, matrix size=64×64 and slice thickness=3.8 mm. Image reconstruction was performed in Matlab on a 3.4 GHz PC.

Figure 8:
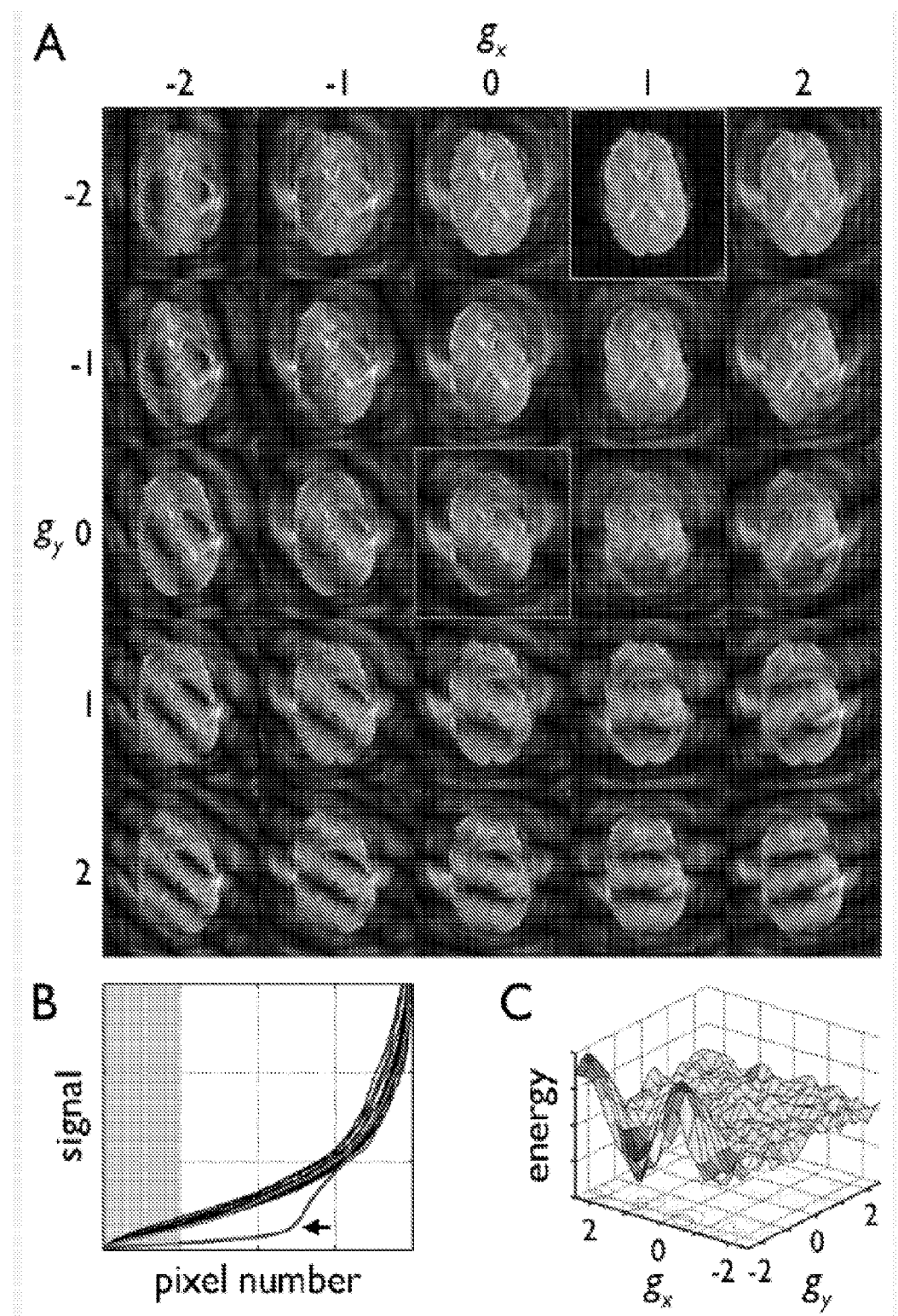
FIG. 8A are panels of images reconstructed using different $g_x$ and $g_y$ values according to embodiments of the present invention.
FIG. 8B is a graph of signal versus pixel number of sorted signal intensity of each image in FIG. 8A according to embodiments of the present invention.
FIG. 8C is a graph of energy as a function of $g_x$ and $g_y$.

FIG. 8A illustrates images reconstructed using different $g_x$ and $g_y$ values. FIG. 8B illustrates a sorted signal intensity of each image and FIG. 8C illustrates background energy as a function of $g_x$ and $g_y$.

The uncorrected image (FIG. 8A, central square) as well as representative images reconstructed at full resolution using different $g_x$ and $g_y$ values have very different aliasing patterns. The sorted signal intensity (FIG. 8B) shows that one of these images has the lowest signal in the background [(gx, gy)=(1,−2), upper row highlighted box] as compared to the uncorrected image [(gx, gy)=(0, 0), center box] or any other image (black outline boxes). A plot of the background energy as a function of $g_x$ and $g_y$ shows that the minimum energy is reached for $(g_x, g_y)$=(1,−2) (in units of k-space line shift) (FIG. 8C). These results confirm that the background energy minimization can indeed identify the image with the least amount of aliasing (FIG. 8A, top square on right side, (1, −2 location)). Similar results can be obtained when cycling through $φ_0$.

By performing the phase cycling at a lower resolution of 16×16, the computation time per slice can be reduced, typically from about 100 h to about 1 h. In addition, by using five iterations of phase cycling with a variable step size rather than a single iteration, the computation time is further reduced to 13 s, which represents a total reduction by a factor $3×10^4$.

These results demonstrate that the proposed iterative phase cycling method can effectively and efficiently correct for motion-induced phase errors in multishot spiral imaging without requiring any additional navigator. It is also contemplated that the methods can be used for multishot spiral DTI.

Figure 9A:
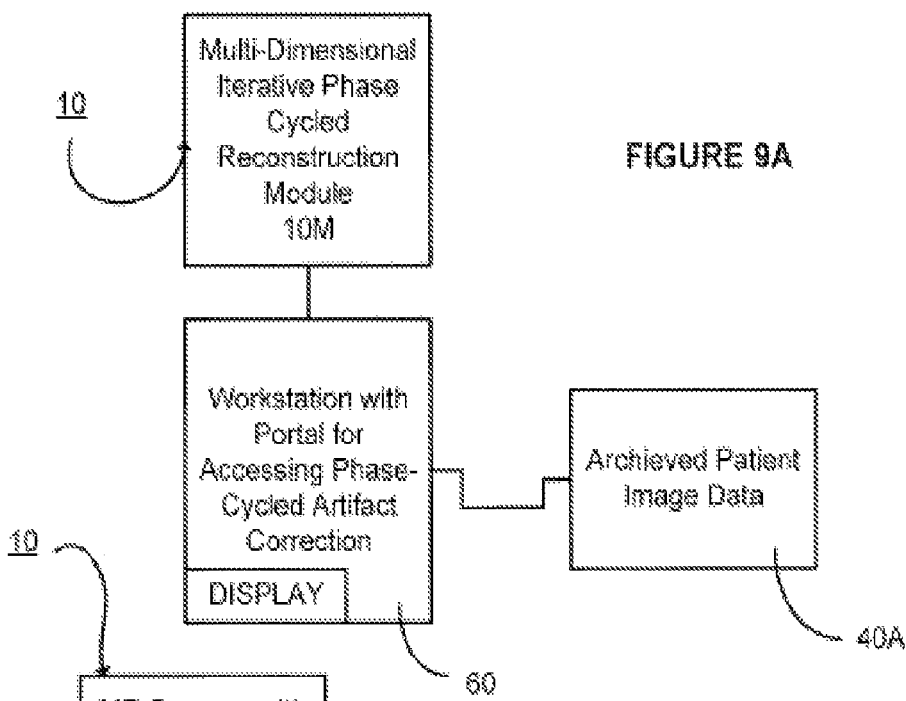
FIGS. 9A-9C are schematic illustrations of different systems that include or communicate with image processing circuits configured to carry out iterative phase-cycled reconstruction to reduce artifact errors according to embodiments of the present invention.
Figure 9B:
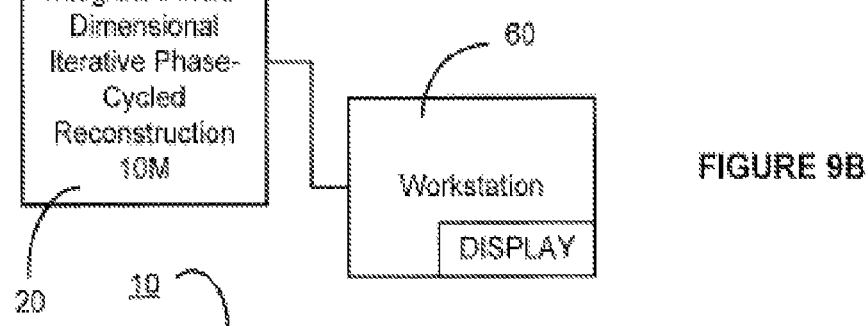
Figure 9C:
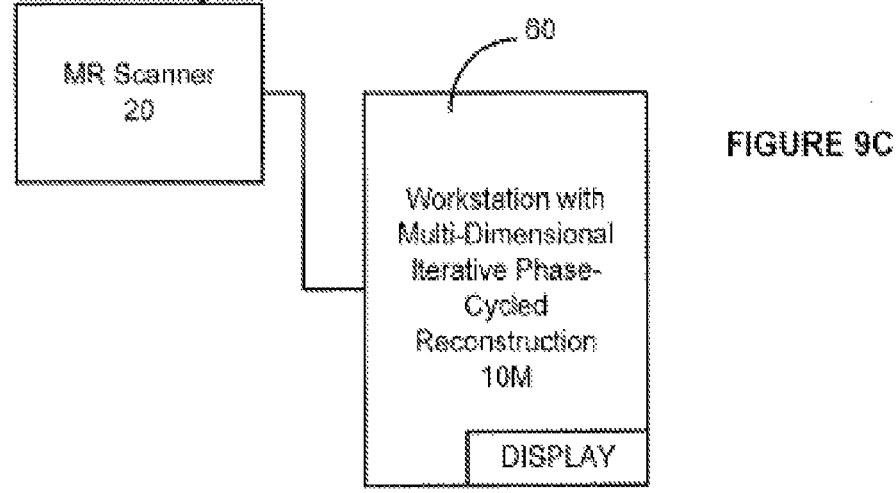

FIGS. 9A-9C illustrate exemplary image processing systems 10 with a multi-dimensional iterative phase-cycling artifact correction module or circuit 10M.

FIG. 9A illustrates that the system 10 can include at least one workstation 60 that has a portal for accessing the module 10M. The module 10M can be held on a remote server accessible via a LAN, WAN or Internet. The workstation 60 can communicate with archived patient image data 40A which may be held in a remote or local server or other electronically accessible database or repository. The workstation 60 can include a display with a GUI (graphic user input) and the access portal. The system 10 can communicate with or be integrated into a PACS system. In particular embodiments, as known to those of skill in the art, the system 10 can include at least one server with an image import module, patient data storage 40A, a data fetch module, a client workstation 60 and a rendering system. The workstation 60 can allow interactive collaboration of image rendering to give the physician alternate image views of the desired features. The rendering system can be configured to zoom, rotate, and otherwise translate to give the physician visualization of the patient data in one or more views, such as section, front, back, top, bottom, and perspective views. The rendering system may be wholly or partially incorporated into the physician workstation 60, or can be a remote or local module (or a combination remote and local module) component or circuit that can communicate with a plurality of physician workstations (not shown). The visualization system 10 can employ a computer network and may be particularly suitable for clinical data exchange/transmission over an intranet. See, e.g., U.S. Pat. No. 7,689,539, the contents of which are hereby incorporated by reference as if recited in full herein. The workstation can access the data sets via a relatively broadband high speed connection using, for example, a LAN or may be remote and/or may have lesser bandwidth and/or speed, and for example, may access the data sets via a WAN and/or the Internet. Firewalls may be provided as appropriate for security.

FIG. 9B illustrates that the module 10M can be included in the MR Scanner 20 which can communicate with a workstation 60. The module 10M can be integrated into the control cabinet with image processing circuitry. FIG. 9C illustrates that the module 10M can be integrated into one or more local or remote workstations 60 that communicates with the Scanner 20. Although not shown, parts of the module 10M can be held on both the Scanner 20 and one or more workstations 60, which can be remote or local.

Figure 10:
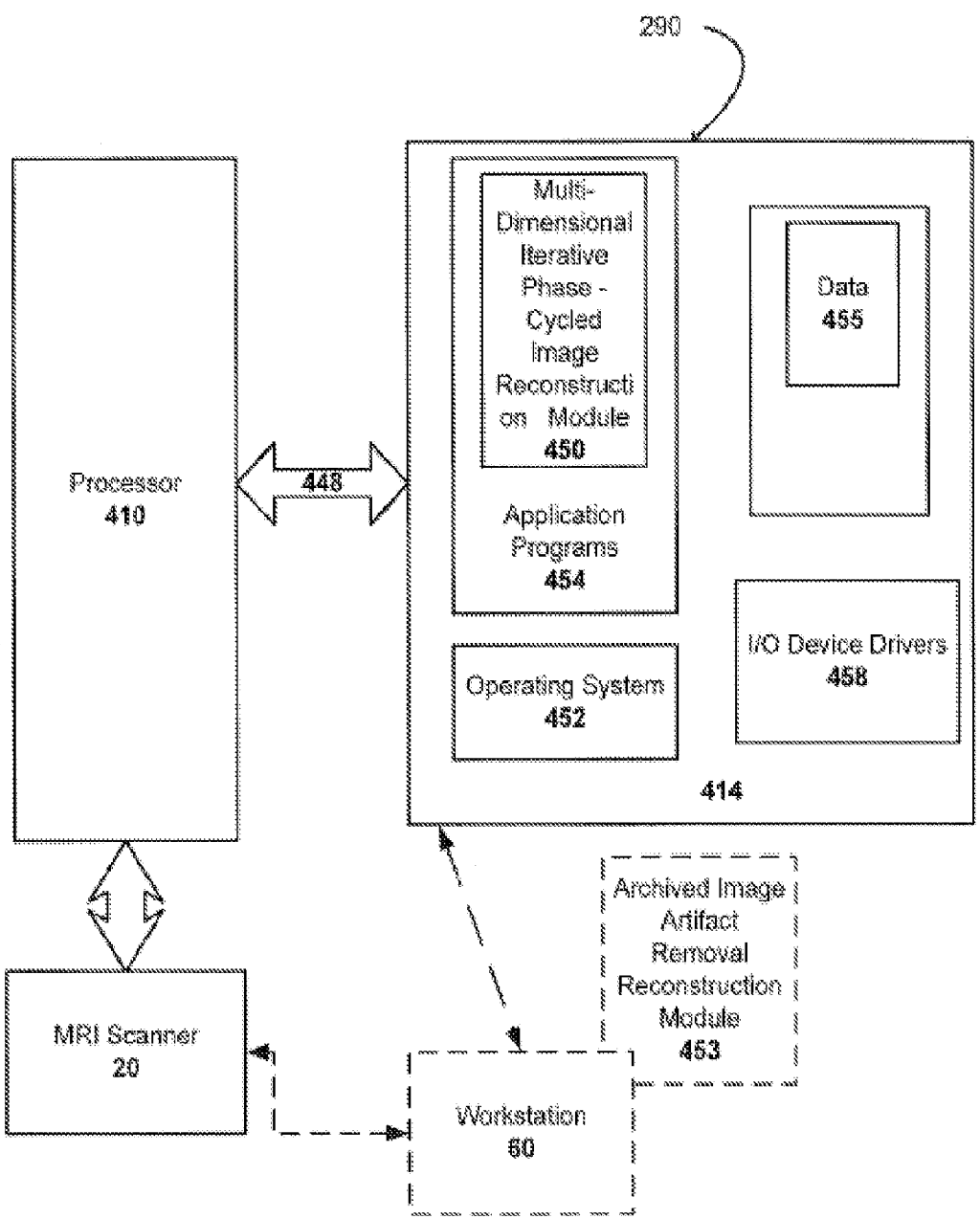
FIG. 10 is a schematic illustration of a data processing system according to embodiments of the present invention.

FIG. 10 is a schematic illustration of a circuit or data processing system 290. The system 290 can be used with any of the systems 10 and provide all or part of the module 10M. The circuits and/or data processing systems 290 data processing systems may be incorporated in a digital signal processor in any suitable device or devices. As shown in FIG. 10, the processor 410 can communicate with an MRI scanner 20 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 10 illustrates that the memory 414 may include several categories of software and data used in the data processing system: the operating system 452; the application programs 454; the input/output (I/O) device drivers 458; and data 455. The data 455 can include patient-specific MRI image data. FIG. 10 also illustrates the application programs 454 can include a Multi-Dimensional, Iterative Phase-Cycled Image Reconstruction Module 450. Optionally, the circuit 290 and/or workstation 60 can be in communication with (e.g., include an interface or access portal or the like) or comprise an archieved-image artifact removal reconstruction module 453.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Module 450 being an application program in FIG. 10, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 10 which is intended to encompass any configuration capable of carrying out the operations described herein. Further, Module 450 can communicate with or be incorporated totally or partially in other components, such as an MRI scanner 20, interface/gateway or workstation 60.

The I/O data port can be used to transfer information between the data processing system, the workstation, the MRI scanner, the interface/gateway and another computer system or a network (e.g., the Internet) or to other devices or circuits controlled by the processor. These components may be conventional components such as those used in many conventional data processing systems, which may be configured in accordance with the present invention to operate as described herein.

Figure 11:
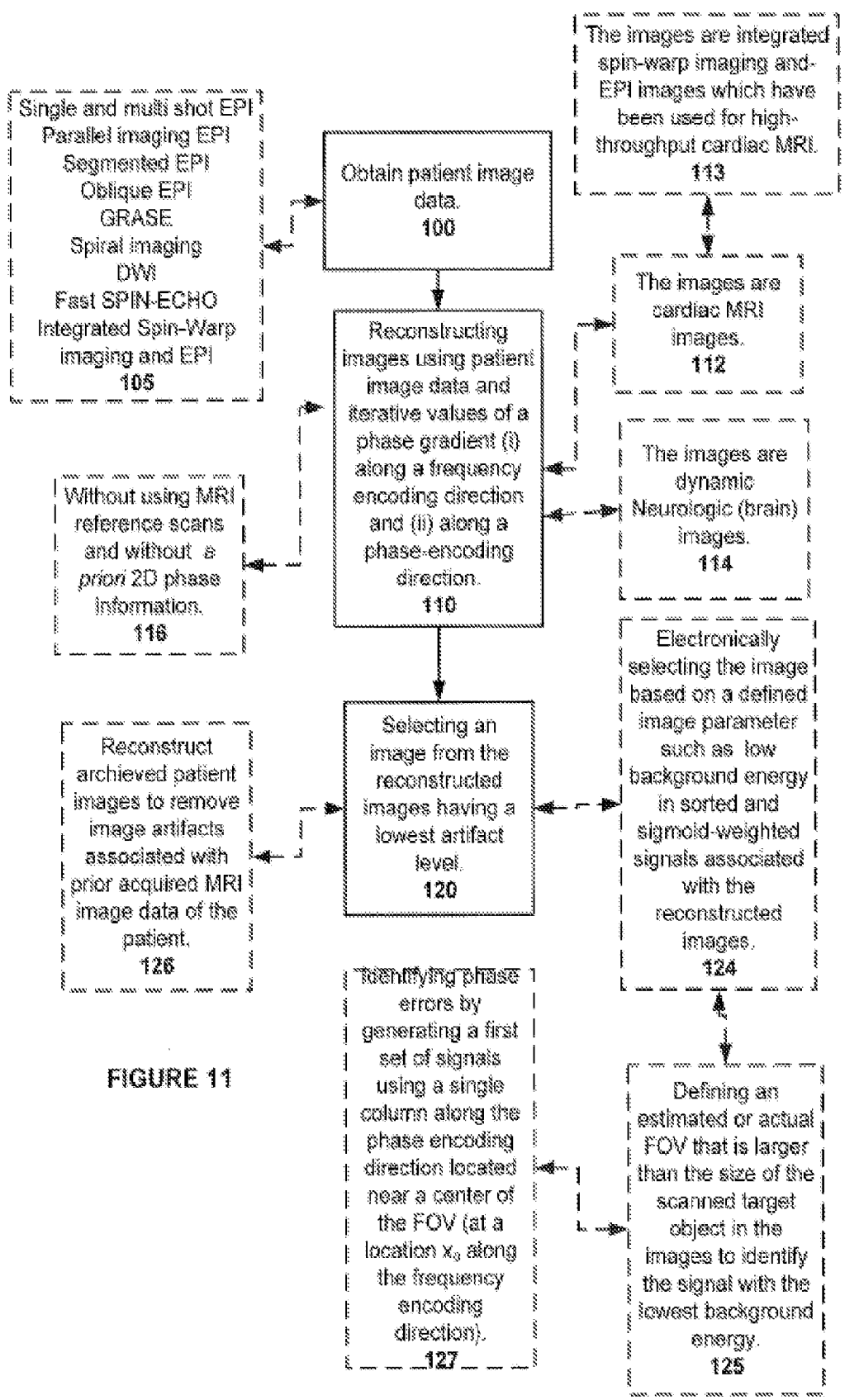
FIG. 11 is a flow chart of exemplary operations that can be used to carry out actions or methods contemplated by embodiments of the present invention to reduce artifact errors in MR images.

FIG. 11 is a flow chart of exemplary actions that can be used to carry out methods according to embodiments of the present invention. Patient image data is obtained (block 100). The patient image data can be archived patient image data to remove image artifacts associated with prior acquired MRI image data of the patient (block 126).

In particular embodiments, the image data can correspond to cardiac MRI images (block 112) or neurologic (brain) images such as dynamic neurologic (brain) images (block 114). The pulse sequences or acquisition protocol can include one or more of: single and multi shot EPI, parallel imaging EPI, segmented EPI, oblique EPI, GRASE, spiral imaging, DWI, fast spin-echo and integrated spin-warp imaging and EPI (block 105).

The methods can include reconstructing images using patient image data and iterative values of a phase gradient (i) along a frequency encoding direction and (ii) along a phase-encoding direction (block 110). This can be carried out without requiring or using MRI reference scans and without a priori 2D phase information (block 116). An image from the reconstructed images having a lowest artifact level can be identified (block 120). This image can be used to identify phase error patterns.

The lowest artifact level image can be electronically selected based on a defined image parameter such as low background energy in sorted and sigmoid-weighted signals associated with the reconstructed images (block 124).

To aid in the identification, an estimated or actual FOV that is larger than the size of the scanned target object in the images is used to identify the signal with the lowest background energy (block 125).

In some embodiments, the phase errors can be identified by generating a first set of signals (pixel intensity) along the phase encoding direction located near a center of the FOV (e.g., at a location "$x_o$" along the frequency encoding direction) (block 127). This set can be associated with a single column of an inversion matrix that has multiple columns associated with an image slice. Other sets of images can be generated for the other columns using the same phase values and iterative step or a smaller range and a different iterative step value.

The generating step can include generating 1D MRI signal profiles using image data corresponding to a center FOV location and the identifying step can be carried out by: (a) electronically sorting the 1D signal profiles in ascending order, (b) multiplying the sorted signal profiles by a sigmoid function (to suppress signals in greater than 50% FOV) to define the sigmoid-weighted signals; (c) electronically summing the weighted sorted signal profiles; and (d) electronically identifying a lowest summed 1D signal profile as being an image with a lowest artifact level. Alternatively, the (a) sorting can be in a different order, e.g., a descending order.

The generating step can be carried out so that a first series of reconstructed images is generated using a first phase error range and a first iterative step size and a second series of reconstructed images are subsequently electronically generated using a reduced phase error range and different step size.

Figure 12:
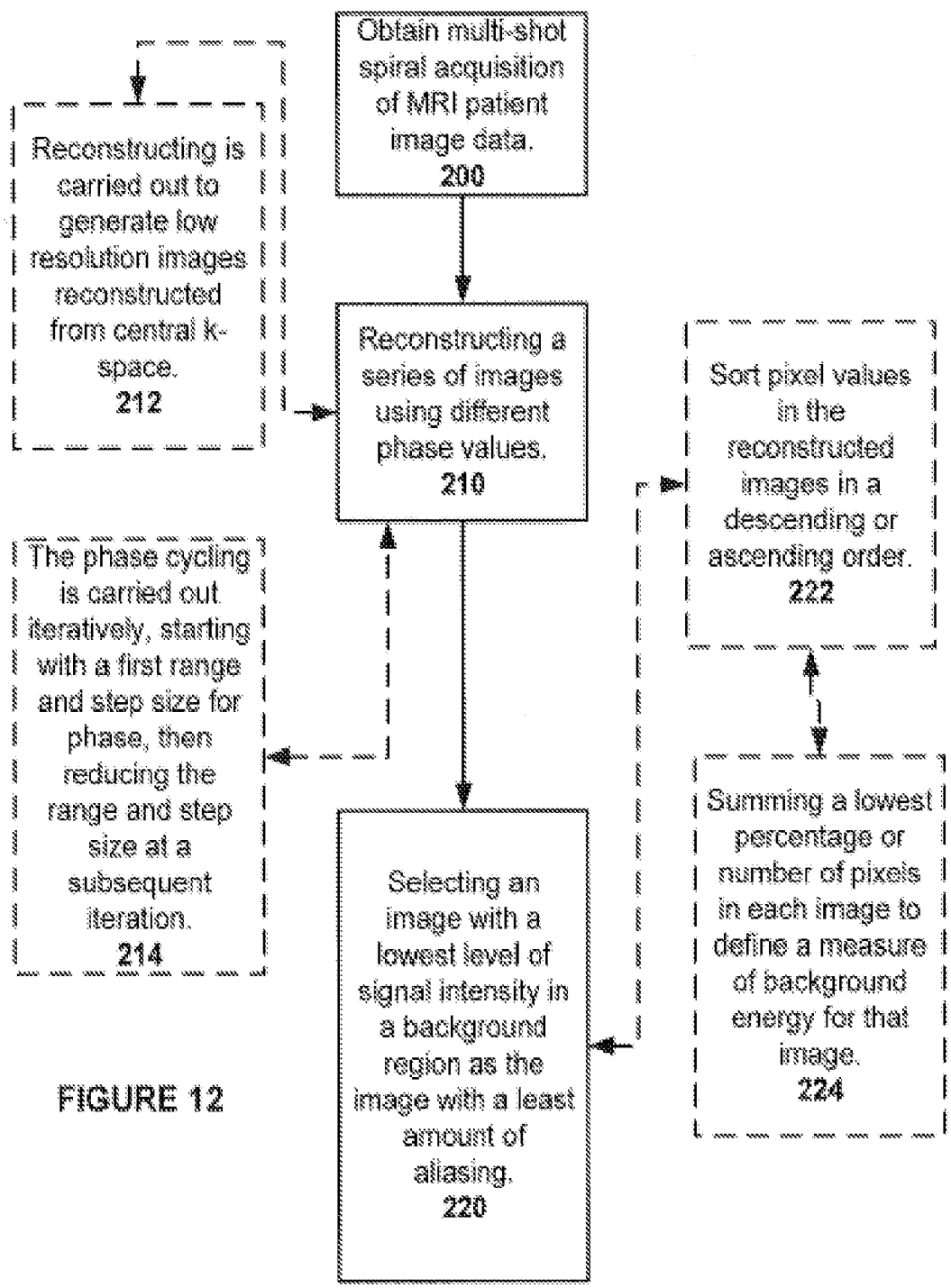
FIG. 12 is another flow chart of exemplary operations that can be used to carry out actions or methods contemplated by embodiments of the present invention to reduce artifact errors in MR images.

FIG. 12 is a flow chart of exemplary actions that can be used to carry out methods according to additional embodiments of the present invention. These actions may be particularly suitable for spiral image data (including spiral DTI). Multi-shot spiral acquisition of MRI patient image data is obtained (block 200). A series of images are reconstructed from central k-space using iterative phase-cycling of different phase values (block 210). An image with a lowest level of signal intensity in a background region is selected as the image with a least amount of aliasing (block 220).

The phase cycling is carried out iteratively, starting with a first range and step size for phase, then reducing the range and step size at a subsequent iteration (block 214). The reconstructing can be carried out to generate low resolution images reconstructed from central k-space (block 212). Pixel values in the reconstructed images can be sorted in an ascending order (block 222). A lowest percentage or number of pixels in each image can be summed to define a measure of background energy for that image (block 224). Alternatively, the pixel values in the images can be sorted in a descending order and a highest percentage can be summed to define the measure of background energy.

In conclusion, it is believed that embodiments of the invention provide the first and general reference-less multi-dimensional (e.g., 2D) phase correction technique, for reducing EPI Nyquist artifacts and/or motion-induced artifacts with no additional navigator for spiral and EPI images. Embodiments can generally be applied to single-shot and segmented EPI and other image sequences as discussed herein. The developed methods are believed to be superior to 1D phase correction, particularly for oblique-plane imaging.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the That which is claimed:

1. A method for generating MRI images with reduced aliasing artifacts in either non-parallel or parallel MRI, comprising:
electronically reconstructing a series of images using patient image data obtained from a patient MRI image data set by iteratively cycling through different estimated values of phase gradients in at least two dimensions; and
electronically selecting an image from the reconstructed images as having a lowest artifact level,
wherein the electronically reconstructing step comprises, for a respective image slice, generating a first series of images using different possible phase gradient values along a frequency encoding direction and a second series of images using different possible values of phase gradients along a phase-encoding direction; the method further comprising:
generating 1D image signal profiles associated with the reconstructed first and second series of images; and
multiplying the 1D image signal profiles by a respective sigmoid-function weight to generate sigmoid-weighted signals,
wherein the electronically selecting step is carried out using the sigmoid-weighted signals to identify phase error patterns.

2. The method of claim 1, wherein the 1D image signal profiles represent background energy in the reconstructed images.

3. The method of claim 1, wherein the reconstructing step is carried out without acquiring reference scans or without requiring user input to identify background regions in the images.

4. The method of claim 1, wherein the generating and identifying steps are carried out to suppress, correct or remove Nyquist ghost artifacts, motion-induced artifacts or other types of aliasing artifacts from the patient images acquired with either non-parallel or parallel MRI.

5. The method of claim 1, wherein the reconstructing image step is carried out using a defined phase range of values and a defined step size in a change in the estimated values of phase gradients (i) along the frequency encoding direction and (ii) along the phase-encoding direction.

6. The method of claim 1, wherein the reconstructing step comprises generating a first series of images using a selected first column of image data along the phase encoding direction located near a center of a field of view (FOV) at a defined location along the frequency encoding direction, then generating a second series of images using an adjacent second column of image data with a different range of phase values and a different step size in change between phase values.

7. The method of claim 6, wherein phase errors $\phi$ in the selected first column along the phase encoding (y) direction and location $x_o$ along the frequency-encoding direction, can be represented using at least $C_1$ and $C_2$ identified by the following equation:

$$\phi(x_0,y)=C_1+C_2 \times y$$

where $C_1$ includes a contribution from both 1) a phase offset that is uniform for the whole 2D image and 2) nonlinear phase terms along the frequency-encoding direction, and $C_2$ represents a linear phase gradient along the phase encoding direction.

8. The method of claim 6, wherein phase errors $\phi$ in the selected first column along the phase encoding (y) direction and location $x_0$ along the frequency-encoding direction, can be represented using the following equation:

$$\phi(x_0,y)=C_1+C_2 \times y+C_3 \times y^2$$

where $C_1$ includes a contribution from both 1) a phase offset that is uniform for a whole 2D image and 2) nonlinear phase terms along the frequency-encoding direction, $C_2$ represents a linear phase gradient along the phase encoding direction, and $C_3$ represents a nonlinear phase gradient along the phase-encoding direction.

9. The method of claim 1, wherein the generating step comprises generating multiple sets of 1D signal profiles based on different possible values of $C_1$ cycled between $-\pi$ and $+\pi$ per pixel in a defined number "N" of steps and $C_2$ also cycled between $-\pi$ per pixel and $+\pi$ per pixel in the defined number "N" of steps to generate N×N 1D profile signals from the chosen column, where $C_1$ is a variable that includes a contribution from both 1) a phase offset that is uniform for a whole 2D image and 2) nonlinear phase terms along the frequency-encoding direction, and where $C_2$ represents a linear phase gradient along the phase encoding direction.

10. The method of claim 1, further comprising electronically sorting the 1D signal profiles in a defined order before the multiplying step, then multiplying the sorted signal profiles by the respective sigmoid-function weight to define the sigmoid-weighted signals;
electronically summing the weighted sorted signal profiles; and
electronically identifying a lowest summed 1D signal profile as being an image with a lowest artifact level,
wherein the elctronically selecting is carried out by identifying a phase error pattern associated with a column corresponding to the lowest summed 1D signal profile.

11. The method of claim 1, wherein the reconstructing step is carried out so that a first series of reconstructed images is electronically evaluated using a first phase error range and iterative step size, and a second series of reconstructed images is subsequently electronically evaluated using a reduced phase error range and an adjusted step size.

12. The method of claim 1, wherein the patient image data is obtained using at least one of the following pulse sequences:
single-shot EPI, segmented EPI, parallel EPI, GRASE, multi-shot spiral imaging, fast spin-echo imaging, and integration of spin-warp imaging and EPI.

13. A method of generating images from multi-shot EPI or spiral imaging with corrected motion-induced phase errors, comprising:
obtaining multi-shot EPI or spiral acquired MRI patient image data;
iteratively phase cycling images of the obtained MRI patient image data reconstructed from central k-space, wherein the iterative phase cycling comprises, for a respective image slice, generating a first series of images using different possible phase gradient values along a frequency encoding direction and a second series of images using different possible values of phase gradients along a phase-encoding direction;
generating 1D image signal profiles associated with the first and second series of images; and
multiplying the 1D image signal profiles by a respective sigmoid-function weight to generate sigmoid-weighted signal profiles;
selecting an image with a lowest level of signal intensity in a background region as the image with a least amount of aliasing using the sigmoid-weighted signal profiles to identify phase error patterns; and generating a patient image based on the selected image.

14. The method of claim 13, wherein the phase cycling is carried out iteratively starting with a first range and step size at a first iteration, then reducing the range and adjusting the step size at a subsequent iteration.

15. The method of claim 13, wherein the iterative phase cycling reconstructions are carried out by reconstructing low resolution images from central k-space, and wherein the generating step is carried out to generate a higher resolution patient image.

16. The method of claim 13, further comprising sorting pixel values associated with background energy in the reconstructed images in a defined order.

17. The method of claim 16, wherein the sorting is in an ascending order, the method further comprising summing a lowest percentage or number of pixels in each image to define a measure of background energy for that image.

18. The method of claim 13, wherein the obtained patient image data are from diffusion-weighted spiral imaging.

19. An image processing circuit configured to (a) electronically perform iterative phase-cycled image reconstruction in at least two dimensions on MRI patient image data sets to generate MRI images with reduced aliasing artifacts without a reference scan, wherein the iterative phase-cycled reconstruction can be applied to MRI patient image data to suppress multi-dimensional phase errors in either image-domain or k-space domain, and (b) electronically select an image from the reconstructed images as having a lowest artifact level, wherein the iterative phase-cycled image reconstruction comprises, for a respective image slice, generating a first series of images using different possible phase gradient values along a frequency encoding direction and a second series of images using different possible values of phase gradients along a phase-encoding direction, generating 1D image signal profiles associated with the first and second series of images, and multiplying the 1D image signal profiles by a respective sigmoid-function weight to generate sigmoid-weighted signal profiles, wherein the electronically selecting step is carried out using the sigmoid-weighted signal profiles to identify phase error patterns.

20. The circuit of claim 19, wherein the circuit is at least partially integrated into or in communication with at least one of: (a) a MR Scanner; (b) a clinician workstation; or (c) Picture Archiving and Communication System with archived patient image data.

21. The circuit of claim 19, wherein the image processing circuit is configured to sort the sigmoid-function weighted signal profiles to identify phase pattern errors and correct for Nyquist artifacts.

22. The circuit of claim 19, wherein the image processing circuit is configured to reconstruct low resolution image slices by iteratively phase cycling images of the obtained MRI patient image data from central k-space, then select an image with a lowest level of signal intensity in a background region as an image with a least amount of aliasing using the sigmoid-function weighted signal profiles, and generate a patient image based on the selected image.

23. The circuit of claim 22, wherein the iterative phase cycling is carried out starting with a first range and step size at a first iteration, then reducing the range and adjusting the step size at a subsequent iteration.

24. An MR image processing system, comprising:

a clinician workstation with a display and user interface comprising or being in communication with at least one image processing system configured to (a) electronically perform multi-dimensional iterative phase-cycled image reconstruction on MRI patient image data sets to generate MRI images with reduced artifacts without a reference scan, wherein the iterative phase-cycled reconstruction can be applied to MRI patient image data sets to suppress multi-dimensional phase errors in either image-domain or k-space domain, and (b) electronically select an image from the reconstructed images as having a lowest artifact level, wherein the iterative phase-cycled image reconstruction comprises, for a respective image slice, generating a first series of images using different possible phase gradient values along a frequency encoding direction and a second series of images using different possible values of phase gradients along a phase-encoding direction, generating 1D image signal profiles associated with the first and second series of images, and multiplying the 1D image signal profiles by a respective sigmoid-function weight to generate sigmoid-weighted signal profiles, wherein the electronically selecting step is carried out using the sigmoid-weighted signal profiles to identify phase error patterns.

25. The system of claim 24, further comprising an MR Scanner in communication with the workstation.

26. The system of claim 24, wherein the workstation is in communication with a Picture Archiving and Communication System with archived patient MR image data.

27. A data processing system comprising non transitory computer readable storage medium having computer readable program code embodied in the medium, the computer-readable program code comprising computer readable program code performs multi-dimensional iterative phase-cycled image reconstruction on MRI patient image data sets to generate MRI images with reduced artifacts and without a reference scan, and selects an image from the reconstructed images as having a lowest artifact level, wherein the computer readable program code that performs the iterative phase-cycled image reconstruction is configured to, for a respective image slice, generate a first series of images using different possible phase gradient values along a frequency encoding direction and a second series of images using different possible values of phase gradients along a phase-encoding direction, generate 1D image signal profiles associated with the first and second series of images, and multiply the 1D image signal profiles by a respective sigmoid-function weight to generate sigmoid-weighted signals, and wherein the computer readable program code that selects the image with the lowest artifact level uses the sigmoid-weighted signals to identify phase error patterns.

28. The method of claim 1, wherein the patient image data includes 1D phase corrected data using a 1D reference scan.

29. An image processing circuit, wherein the image processing circuit (a) electronically performs: iterative phase-cycled image reconstruction in at least two dimensions on (i) MRI patient image data sets without a reference scan or on (ii) MRI patient image data that have been 1D phase corrected based on a reference scan, wherein the iterative phase-cycled reconstruction can be applied to the MRI patient image data to suppress multi-dimensional phase errors in either image-domain or k-space domain to generate MRI images with reduced aliasing artifacts, and (b) electronically selects an image from the reconstructed images as having a lowest artifact level wherein the iterative phase-cycled image reconstruction comprises, for a respective image slice:

generating a first series of images using different possible phase gradient values along a frequency encoding direction and a second series of images using different possible values of phase gradients along a phase-encoding direction;

generating 1D image signal profiles associated with the first and second series of images; and multiplying the 1D image signal profiles by a respective sigmoid-function weight to generate sigmoid-weighted singals, wherein the circuit electronically selects the image having the lowest artifact level using the sigmoid-weighted signals to identify phase error patterns.

30. An MR image processing system, comprising:
a clinician workstation with a display and user interface comprising or being in communication with at least one image processing system configured to; (a) electronically perform multi-dimensional iterative phase-cycled image reconstruction on MRI patient image data sets to generate MRI images with reduced artifacts, wherein the iterative phase-cycled reconstruction can be applied to MRI patient image data sets to suppress multi-dimensional phase errors in either image-domain or k-space domain; and (b) electronically select an image from the reconstructed images as having a lowest artifact level, and wherein the electronic iterative phase-cycled image reconstruction comprises, for a respective image slice, generating a first series of images using different possible phase gradient values along a frequency encoding direction, generating a second series of images using different possible values of phase gradients along a phase-encoding direction, generating 1D image signal profiles associated with the first and second series of images, and multiplying the 1D image signal profiles by a respective sigmoid-function weight to generate sigmoid-weighted signals, wherein the electronic selection uses the sigmoid-weighted signals to identify phase error patterns.

31. The system of claim 30, wherein the image processing system is configured to perform the multi-dimensional iterative phase-cycled image reconstruction on MRI patient image data sets without a reference scan.

32. The system of claim 30, wherein the image processing system is configured to perform the multi-dimensional iterative phase-cycled image reconstruction on MRI patient image data that have been 1D phase corrected based on a reference scan.

* * * * *

UNITED STATES PATENT AND TRADEMARK OFFICE
CERTIFICATE OF CORRECTION

Page 1 of 1

PATENT NO. : 8,934,694 B2
APPLICATION NO. : 13/824704
DATED : January 13, 2015
INVENTOR(S) : Chen et al.

It is certified that error appears in the above-identified patent and that said Letters Patent is hereby corrected as shown below:

In the Claims:
Column 30, Claim 27, Line 29: delete "non transitory"
insert -- non-transitory --

Column 30, Claim 27, Line 33: delete "code performs"
insert -- code that performs --

Column 30, Claim 29, Line 56: delete "performs: iterative"
insert -- performs iterative --

Column 30, Claim 29, Line 66: delete "level wherein the"
insert -- level, wherein the --

Column 31, Claim 29, Line 10: delete "singals,"
insert -- signals, --

Column 32, Claim 30, Line 2: delete "and wherein the"
insert -- wherein the --

Signed and Sealed this
Twenty-fifth Day of August, 2015

Michelle K. Lee
*Director of the United States Patent and Trademark Office*